US012594195B2

(12) United States Patent (10) Patent No.: US 12,594,195 B2
Ljungberg et al. (45) Date of Patent: Apr. 7, 2026

(54) DISPOSABLE PANT ARTICLE AND METHOD FOR PRODUCING DISPOSABLE PANT ARTICLES

(71) Applicant: Essity Hygiene and Health Aktiebolag, Gothenburg (SE)

(72) Inventors: Karin Ljungberg, Gothenburg (SE); Katarina Eriksson, Gothenburg (SE); Lucas Bäck, Gothenburg (SE); Anna Stenberg, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 1049 days.

(21) Appl. No.: 17/051,317

(22) PCT Filed: Jun. 5, 2018

(86) PCT No.: PCT/EP2018/064759
§ 371 (c)(1),
(2) Date: Oct. 28, 2020

(87) PCT Pub. No.: WO2019/233564
PCT Pub. Date: Dec. 12, 2019

(65) Prior Publication Data
US 2021/0093485 A1 Apr. 1, 2021

(51) Int. Cl.
*A61F 13/15* (2006.01)
*A61F 13/496* (2006.01)
(Continued)

(52) U.S. Cl.
CPC ...... *A61F 13/15203* (2013.01); *A61F 13/496* (2013.01); *A61F 13/51394* (2013.01); *A61F 13/51496* (2013.01); *A61F 13/53* (2013.01)

(58) Field of Classification Search
CPC .............. A61F 13/15203; A61F 13/496; A61F 13/51394; A61F 13/51496; A61F 13/53;
(Continued)

(56) References Cited

U.S. PATENT DOCUMENTS

| | | | |
|---|---|---|---|
| 4,834,735 A | 5/1989 | Alemany et al. | |
| 8,378,165 B2 | 2/2013 | Visscher et al. | |
| | (Continued) | | |

FOREIGN PATENT DOCUMENTS

| | | | |
|---|---|---|---|
| AU | 2007326875 A1 | 6/2008 | |
| CN | 1599584 A | 3/2005 | |
| | (Continued) | | |

OTHER PUBLICATIONS

Office Action (Decision of Rejection) issued on May 16, 2022, by the Japanese Patent Office in corresponding Japanese Patent Application No. 2021-517109, and an English Translation of the Office Action. (7 pages).

(Continued)

*Primary Examiner* — Rebecca E Eisenberg
*Assistant Examiner* — Brandon W. Levy
(74) *Attorney, Agent, or Firm* — BUCHANAN INGERSOLL & ROONEY PC

(57) ABSTRACT

Disposable pant article having a waist portion and a crotch portion includes an absorbent core and a liquid-permeable topsheet covering the absorbent core, wherein the article is composed of a plurality of fabrics which define the colours of the inside and outside surfaces of the article. At least the outside surface and a surrounding zone, surrounding the absorption zone, have, in the CIE L*a*b* colour space, L* values less than 80 and mutual colour differences ΔE*ab less than 10; and the absorption zone has, in the CIE L*a*b* colour space, an L* value less than 90 and a colour differ- (Continued)

ence ΔE*ab more than 5 with respect to the surrounding zone and/or the outer surface.

19 Claims, 10 Drawing Sheets

(51) Int. Cl.
| | | |
|---|---|---|
| *A61F 13/513* | (2006.01) | |
| *A61F 13/514* | (2006.01) | |
| *A61F 13/53* | (2006.01) | |

(58) Field of Classification Search
CPC .......... A61F 13/15577; A61F 13/49007; A61F 2013/15243; A61F 2013/8497; A61F 2013/51377; A61F 2013/4708; A61F 13/84; A61F 13/47254; A61F 13/47; A61F 13/511
See application file for complete search history.

(56) References Cited

U.S. PATENT DOCUMENTS

| | | | |
|---|---|---|---|
| 8,492,609 B2 | 7/2013 | Ecker et al. | |
| 8,652,113 B2 | 2/2014 | Gabrielii et al. | |
| 9,060,902 B2 | 6/2015 | Gabrielii et al. | |
| 9,259,367 B2 | 2/2016 | Magee et al. | |
| 9,456,932 B2 | 10/2016 | Digiacomantonio et al. | |
| 9,737,441 B2 | 8/2017 | Song et al. | |
| 10,226,385 B2 | 3/2019 | Rosati et al. | |
| 10,687,993 B2 | 6/2020 | Rudén et al. | |
| 2003/0028166 A1 | 2/2003 | Price et al. | |
| 2003/0114809 A1* | 6/2003 | Gagliardi .......... | A61F 13/15203 604/385.01 |
| 2003/0114811 A1 | 6/2003 | Christon et al. | |
| 2005/0145523 A1* | 7/2005 | Zander .............. | A61F 13/51496 206/438 |
| 2006/0025737 A1 | 2/2006 | Song et al. | |
| 2009/0275911 A1 | 11/2009 | Hormung et al. | |
| 2010/0108554 A1 | 5/2010 | Melius et al. | |
| 2012/0226249 A1 | 9/2012 | Prodoehl et al. | |
| 2012/0323204 A1* | 12/2012 | Poole ............... | A61F 13/49011 604/385.01 |
| 2016/0270976 A1 | 9/2016 | Minoguchi et al. | |
| 2017/0058140 A1 | 3/2017 | Imamura et al. | |
| 2021/0093485 A1 | 4/2021 | Ljungberg et al. | |
| 2021/0369510 A1 | 12/2021 | Ljungberg et al. | |

FOREIGN PATENT DOCUMENTS

| | | | |
|---|---|---|---|
| CN | 1625380 A | 6/2005 | |
| CN | 101292930 A | 10/2008 | |
| CN | 101410078 A | 4/2009 | |
| CN | 101677879 A | 3/2010 | |
| CN | 101677884 A | 3/2010 | |
| CN | 102202620 A | 9/2011 | |
| CN | 102202628 A | 9/2011 | |
| CN | 107106379 A | 8/2017 | |
| CO | 2018011791 A2 | 1/2019 | |
| EP | 1108406 A2 | 6/2001 | |
| EP | 1252873 A2 | 10/2002 | |
| EP | 1704842 A1 | 9/2006 | |
| JP | 2003070838 A | 3/2003 | |
| JP | 2004504106 A | 2/2004 | |
| JP | 2007050145 A | 3/2007 | |
| JP | 2008522770 A | 7/2008 | |
| JP | 2012507337 A | 3/2012 | |
| JP | 2014226216 A | 12/2014 | |
| JP | 5784851 B1 | 9/2015 | |
| JP | 2016073511 A | 5/2016 | |
| JP | 2017050145 A | 3/2017 | |
| JP | 2017104438 A | 6/2017 | |
| KR | 20030022297 A | 3/2003 | |
| RU | 2611280 C2 | 2/2017 | |

| | | | | |
|---|---|---|---|---|
| WO | 02-07661 A2 | 1/2002 | | |
| WO | 02-07662 A1 | 1/2002 | | |
| WO | 02096331 A2 | 12/2002 | | |
| WO | 03047488 A1 | 6/2003 | | |
| WO | 2005-044164 A1 | 5/2005 | | |
| WO | 2005122985 A1 | 12/2005 | | |
| WO | 2006-015206 A2 | 2/2006 | | |
| WO | 2006015207 A2 | 2/2006 | | |
| WO | 2007-017817 A2 | 2/2007 | | |
| WO | WO-2007024327 A1 * | 3/2007 | ....... | A61F 13/51456 |
| WO | 2007133127 A1 | 11/2007 | | |
| WO | 2008065627 A2 | 6/2008 | | |
| WO | 2009-031393 A1 | 3/2009 | | |
| WO | 2010050853 A1 | 5/2010 | | |
| WO | 2010050854 A1 | 5/2010 | | |
| WO | 2011-125530 A1 | 10/2011 | | |
| WO | 2011-126088 A1 | 10/2011 | | |
| WO | 2013-021651 A1 | 2/2013 | | |
| WO | 2016068764 A1 | 5/2016 | | |
| WO | 2016182484 A1 | 11/2016 | | |
| WO | 2017-082834 A1 | 5/2017 | | |
| WO | 2018097770 A1 | 5/2018 | | |

OTHER PUBLICATIONS

International Search Report (PCT/ISA/210) and Written Opinion (PCT/ISA/237) mailed on Feb. 28, 2019, by the European Patent Office as the International Searching Authority for International Application No. PCT/EP2018/064759.

Examination report issued in corresponding Australian Patent Application No. 2018426934, dated Jul. 8, 2021. (3 pages).

Office Action (Decision of Rejection) issued on Jul. 8, 2022, by the Chinese Patent Office in corresponding Chinese Patent Application No. 201880093693.X, and an English Translation of the Office Action. (25 pages).

Office Action issued on Jul. 29, 2022, by the Colombian Patent Office in corresponding Colombian Patent Application No. NC 2020/0015251. (5 pages).

Office Action (Decision of Rejection) issued on May 9, 2022, by the Chinese Patent Office in corresponding Chinese Patent Application No. 201880093697.8., and an English Translation of the Office Action, references previously submitted. (16 pages).

Office Action issued on Apr. 5, 2022, by the Chilean Patent Office in corresponding Chilean Patent Application No. 2020-003154, references previously submitted. (20 pages).

The Examiner's attention is directed to co-pending U.S. Appl. No. 17/051,334, filed Oct. 28, 2020, by Karin Ljunberg et al.

Office Action issued on Nov. 11, 2022, by the Colombian Patent Office in corresponding Colombian Patent Application No. NC 2020/001525, and an English Translation of the Office Action. (22 pages).

First Office Action issued on Aug. 10, 2021, by the Chinese Patent Office in corresponding Chinese Patent Application No. 201880093697. 8, and an English Translation of the Office Action. (25 pages).

Office Action issued on Sep. 16, 2021, by the Chilean Patent Office in corresponding Chilean Patent Application No. 2020-003154. (20 pages; the Chilean IDS includes only issues of clarity).

Office Action issued on Jun. 15, 2021, by the Russian Patent Office in corresponding Russian Patent Application No. 2020141039, and an English Translation of the Office Action. (11 pages).

Notification of the Third Office Action issued on Mar. 22, 2022, by the Chinese Patent Office in corresponding Chinese Patent Application No. 201880093693.X, and an English Translation of the Office Action. (28 pages).

Office Action (Notice of Reasons for Rejection) issued on Feb. 7, 2022, by the Japanese Patent Office in corresponding Japanese Patent Application No. 2020-567806, and an English Translation of the Office Action. (8 pages).

Office Action (Notice of Reasons for Rejection) issued on Jan. 24, 2022, by the Japanese Patent Office in corresponding Japanese Patent Application No. 2021-517109, and an English Translation of the Office Action. (8 pages).

(56)          References Cited

OTHER PUBLICATIONS

Office Action issued on Feb. 18, 2022, by the Canadian Patent Office in corresponding Canadian Patent Application No. 3,101,045. (4 pages).
Second Office Action issued on Dec. 28, 2021, by the Chinese Patent Office in corresponding Chinese Patent Application No. 201880093697.8, and an English Translation of the Office Action. (22 pages).
Notification of First Office Action issued on Aug. 2, 2021, by the Chinese Patent Office in corresponding Chinese Patent Application No. 201880093693, and an English Translation of the Office Action. (31 pages).
Office Action (Examination Report No. 1) issued on May 26, 2021, by the Australian Patent Office in corresponding Australian Patent Application No. 2018426939. (3 pages).
International Search Report (PCT/ISA/210) mailed on Feb. 28, 2019, by the European Patent Office as the International Searching Authority for International Application No. PCT/EP2018/064788.
Notification of Transmittal of the International Preliminary Report on Patentability (PCT/IPEA/416) mailed on Sep. 14, 2020, by the European Patent Office as the International Searching Authority for International Application No. PCT/EP2018/064788.
Reply to Written Opinion of the International Preliminary Examining for International Application No. PCT/EP2018/064788 dated Mar. 31, 2020.
Reply to Written Opinion of the International Preliminary Examining for International Application No. PCT/EP2018/064788 dated Jun. 22, 2020.

Written Opinion (PCT/ISA/237) mailed on Feb. 28, 2019, by the European Patent Office as the International Searching Authority for International Application No. PCT/EP2018/064788.
Written Opinion of the International Preliminary Examining Authority (PCT/IPEA/408) mailed on May 11, 2020, by the European Patent Office as the International Searching Authority for International Application No. PCT/EP2018/064788.
Second Office Action issued on Dec. 20, 2021, by the Chinese Patent Office in corresponding Chinese Patent Application No. 201880093693, and an English Translation of the Office Action. (10 pages).
Office Action issued in corresponding Japanese Application No. 2020-567806, mailed on Nov. 21, 2022, 8 pages including 4 pages of English Translation.
Office Action issued in corresponding Japanese Application No. 2021-517109 , mailed on Nov. 11, 2022, 5 pages including 3 pages of English Translation.
Office Action issued in corresponding Korean Application No. 10-2021-7000090 , mailed on Nov. 28, 2022, 7 pages including 3 pages of English Translation.
Office Action (Decision of Rejection) issued on Aug. 7, 2023, in Japanese Patent Application No. 2020-567806 and English translation of the Office Action. (9 pages).
Office Action issued by the U.S. Patent and Trademark Office in the U.S. Appl. No. 17/051,334, mailed Oct. 6, 2023, U.S. Patent and Trademark Office, Alexandria, VA. (72 pages).
Office Action (Decision for Patent Grant) issued on Jul. 24, 2023, in corresponding Korean Patent Application No. 10-2021-7000090 and English translation of the Office Action. (3 pages).

* cited by examiner

DISPOSABLE PANT ARTICLE AND METHOD FOR PRODUCING DISPOSABLE PANT ARTICLES

FIELD OF THE DISCLOSURE

The present disclosure relates to disposable pant articles and a method for producing disposable pant articles.

BACKGROUND ART

Disposable absorbent articles, for example in the form of incontinence liners, baby diapers and sanitary napkins, are well known. The general purpose of such absorbent articles is to absorb, distribute and store various types of body exudates, while providing a high level of comfort and sense of dryness to the wearer during use of the absorbent article. Also, such an absorbent article is configured to prevent the wearer from getting the clothes soiled by such body exudates.

Absorbent articles in the form of incontinence articles are used to protect a wearer against urine leakage. An incontinence article can be configured for example as a pant diaper, a sanitary pant or an incontinence pant adapted for use by a baby, child or adult, male or female user. Also, an incontinence article is designed with an absorption capacity which is adapted to absorb the fluid that is expected to be released into the article when it is worn. Incontinence articles are used to assist persons with incontinence so that they can maintain a normal lifestyle without any inconvenience caused by incontinence.

Prior art incontinence absorbent products are usually white, with or without print. There are also coloured products on the market which are coloured on the outside. However, many prior art products remain very diaper-like and are therefore often disliked by users, who want a discreet product. They do not want to be continuously reminded that they are using an incontinence product and they do not want to show other people that they are using one, while at the same time they want to feel secure when using the products. Hence there is a need for a more discreet product which at the same time makes users feel secure.

WO200615207 discloses a disposable absorbent article comprising a front waist region, a rear waist region, and a crotch region, wherein said absorbent article further comprises at least three discrete elements each comprising at least one visible surface; wherein at least three or more of the visible surfaces comprise an imparted colour wherein said colours are colour matched. Colour matching exists when said colours are contained within a specified CIELab colour space volume, have a specified hue difference, or total colour difference.

SUMMARY OF THE DISCLOSURE

It is a first aim of the present disclosure to provide a more discreet disposable pant article which at the same time makes users feel secure.

It is a second aim of the present disclosure to provide a more underwear-like disposable pant article.

It is a third aim of the present disclosure to provide a coloured disposable pant article which clearly indicates to users which side is the inside.

It is a fourth aim of the present disclosure to provide an advantageous method for producing more discreet and/or underwear-like disposable pant articles.

The disclosure provides, according to a first aspect, a disposable pant article having a waist portion which in use surrounds a user's waist and a crotch portion connecting front and back portions of the waist portion, the crotch portion comprising an absorbent core for absorbing body exudates and a liquid-permeable topsheet which in use faces a user's crotch, the topsheet covering the absorbent core, wherein the article has an inside surface which in use faces the user's skin and an outside surface which is opposite the inside surface and in use faces the user's clothing; wherein the article is composed of a plurality of fabrics which define the colours of the inside and outside surfaces of the article, the liquid-permeable topsheet being one of the fabrics; wherein an absorption zone is defined as the part of the inside surface, on the topsheet, under which the absorbent core is located, and wherein a surrounding zone is defined as the part of the inside surface, on the topsheet, adjacent to and at least partly surrounding the absorption zone; wherein at least the outside surface and said surrounding zone have, in the CIE L*a*b* colour space, L* values less than 80 and mutual colour differences $\Delta E^*ab$ less than 10; and wherein the absorption zone has, in the CIE L*a*b* colour space, an L* value less than 90 and a colour difference $\Delta E^*ab$ more than 5 with respect to said surrounding zone and/or said outer surface.

Due to the colours of the outside surface and the inside surface at least in the area of the surrounding zone being substantially the same, i.e. a $\Delta E^*ab$ less than 10, the pant article of the present disclosure is more uniform in colour. As a result of being more uniform in colour, the pant articles according to the present disclosure can meet a demand for e.g. incontinence articles which have a design such that they resemble regular underwear, while still giving the wearer a sense of security (by indicating presence of the absorbent core). The discreet pant article can give the wearer a higher level of self-confidence, comfort and self-esteem and can provide incontinence protection for users having different lifestyles. The disposable pant article is a disposable absorbent article.

Uniformity in colour is also advantageous from a manufacturing perspective. In order to have a similar coloured outside and at least a partly coloured inside the same material may be used on several places within the absorbent article. The outside may, for example, be provided with an outer coloured non-woven material both in the crotch area and in the waist area. The same non-woven may also be used on the inside of the waist area and as the topsheet. The topsheet may additionally be treated with surfactants to allow more rapid fluid penetration while retaining optimum wetback and fluid retention characteristics. Coloured materials are more expensive per se because the supplier wastes volumes of the material due to the cleaning needed after production of a batch. Furthermore, the use of coloured materials in producing absorbent articles was also avoided due to risk of colour contamination of white layers of the product or subsequent products, which could likewise lead to volumes of articles being scrapped and the need for cleaning after production of a batch of articles. Alternatively, the outer non-woven material may be a thin white or transparent non-woven material with a coloured sheet of material or a coloured material underneath shining through the thin white or transparent non-woven in order to get a coloured product.

In embodiments according to the disclosure, the absorption zone may have a colour difference $\Delta E^*ab$ more than 10 with respect to said surrounding zone and/or said outside surface. A higher $\Delta E^*ab$ is preferred in view of more clearly indicating the absorption zone to the user.

In embodiments according to the disclosure, the absorption zone may have a colour difference $\Delta E^*ab$ less than 40 with respect to said surrounding zone and/or said outside surface. It is preferred that this $\Delta E^*ab$ is not too high in view of discreetness of the article.

In embodiments according to the disclosure, the indication of the absorption zone may be provided by the absorbent core, or at least an upper layer thereof, being visible through the topsheet. This means that the colour difference of the absorption zone, which indicates its presence to the user, may be achieved by the visibility of the core or upper layer thereof, through the topsheet. In this way, the presence of the absorbent core can be indicated to the user without the need of providing print or other indications on the topsheet itself. The whole topsheet material may be coloured. For example, if the topsheet is fully coloured, a lighter coloured core, for example a white core will show through the non-woven topsheet.

In embodiments, the absorbent core, or at least an upper layer thereof which is visible through the topsheet, may be made of a material which has a higher $L^*$ value (i.e. has a lighter colour) than the topsheet.

In embodiments, the absorption zone, as a result of the combination of the colours of the absorbent core and the topsheet, may have a higher $L^*$ value (i.e. have a lighter colour) than said zone surrounding the absorption zone, $\Delta L^*$ between these zones being more than 5, preferably more than 10 and less than 35.

In embodiments, the material of the absorbent core or upper layer thereof may have an $L^*$ value of more than 80, i.e. be of a light colour which may be clearly visible through the topsheet. When measuring the colour of the absorbent core or an upper layer thereof the topsheet may be removed from the absorbent product.

In embodiments according to the disclosure, said outside surface may comprise several outside portions together forming said outside surface and/or said inside surface may comprise several inside surface portions together forming said inner surface. In embodiments, all or substantially all of the outside and inside surface portions, except for said absorption zone, may have $L^*$ values less than 80 and/or mutual colour differences $\Delta E^*ab$ less than 10.

In embodiments according to the disclosure, all or substantially all of the outside and inside surface portions, except for said absorption zone, may have $L^*$ values less than 60 (i.e. have relatively dark colours) and/or mutual colour differences $\Delta E^*ab$ less than 10. Darker colours may be preferred by users for reasons of discreetness and/or more underwear-like appearance.

In embodiments according to the disclosure, all or substantially all of the outside surface portions, except for said absorption zone, may have $L^*$ values less than 60 (i.e. have relatively dark colours), while the inside surface portions other than the surrounding zone (which may be of the same darker colour as the outside) have higher $L^*$ values. In this way, the inside of the article is generally lighter than the outside, which may help the user to distinguish the inside from the outside.

In embodiments according to the disclosure, one of the outer fabrics of the outside surfaces may be a liquid-impermeable backsheet of the crotch portion. The backsheet may be one of the portions of the outside surface.

In embodiments according to the disclosure, one of the portions of the outside surface may be an elastic non-woven laminate forming the waist portion or one of the sheets forming the elastic non-woven laminate. Such an elastic laminate may comprise two non-elastic non-woven materials with elastic means, such as an elastic film and/or elastic strands, sandwiched between the two non-woven materials. Alternatively, elastic non-woven can form the waist portion. At the same time, the elastic laminate or the elastic nonwoven forming the outside surface portions of the waist portion may also form the inside surface portions of the waist portion. The two non-elastic non-woven materials may have substantially same colour. The terms "substantially the same colour" are used throughout the application and it is meant that they have a mutual colour differences $\Delta E^*ab$ less than 10.

In embodiments according to the disclosure, wherein at least one of the fabrics located at the outside surface and/or at least one of the fabrics located at the inside surface may be formed by non-woven fabrics. The topsheet with underlying material may also form a portion of the inside surface.

In embodiments according to the disclosure, other materials may influence the colour of the outside and inside surfaces of the absorbent product. For example, the backsheet may comprise an outer coloured non-woven material. The outer non-woven material is the material facing the garment during use. The non-woven material may be attached to a film which may also be coloured. The film may be arranged between the outer non-woven material and the core in the crotch area. They together may give the absorbent article the outside colour. The same applies for the waist panel. If the waist panel comprises two coloured non-elastic non-woven materials with a coloured elastic film between, the film may influence the colour of the outside surface and/or the inside surface. Alternatively, the outer non-woven material of the backsheet may be thin white or transparent material with a coloured film shining through the thin white or transparent non-woven. Alternatively, the waist panel may comprise two thin white or transparent non-elastic non-woven materials. The elastic film should then be coloured and shine through the nonwoven to give the product it colour.

In a second aspect, which may be combined with the other aspects and embodiments described herein, the disclosure provides a disposable pant article having a waist portion which in use surrounds a user's waist and a crotch portion connecting front and back portions of the waist portion, the crotch portion comprising an absorbent core for absorbing body exudates and a liquid-permeable topsheet which in use faces a user's crotch, the topsheet covering the absorbent core, wherein the article has an inside surface comprising inside surface portions together forming said inside surface which in use faces the user's skin and an outside surface comprising outside surface portions together forming said outside surface which is opposite the inside surface and in use faces the user's clothing, wherein the article is composed of a plurality of fabrics which define the colours of the inside and outside surface portions of the article, the liquid-permeable topsheet being one of the fabrics; wherein the outside surface portions have, in the CIE $L^*a^*b^*$ colour space, $L^*$ values less than 80 and mutual colour differences $\Delta E^*ab$ less than a predetermined limit; and wherein the inside surface portions have, in the CIE $L^*a^*b^*$ colour space, an $L^*$ value less than 90 and mutual colour difference $\Delta E^*ab$ more than said predetermined limit.

The disposable pant articles according to the second aspect are substantially uniform in colour, at least have less colour differences on the outside than on the inside, together with all said outer and inner fabrics being non-white ($L^*$ values less than 80 resp. 90). It has been found that this combination results in a more discreet article and/or a more underwear-like article. The outside surface may be formed by, that is comprise, just as for the disposable article according to the first aspect, the materials/sheets forming the backsheet and/or the materials forming the waist panel. The inside surfaces may be formed by, that is comprise, just as for the disposable article according to the first aspect, the materials/sheets forming the topsheet and/or the materials forming the waist panel.

In embodiments of the second aspect, the predetermined limit may be 10, i.e. the outside surfaces have mutual colour differences $\Delta E*ab$ less than 10 and the inside surfaces have mutual colour differences $\Delta E*ab$ more than 10.

The definitions and features of the disposable pant article of the first aspect is also applicable to the second aspect.

In a further aspect, which may be combined with the other aspects and embodiments described herein, the disclosure provides a method for manufacturing a plurality of disposable pant articles, wherein each article comprises a waist portion which in use surrounds a user's waist and a crotch portion connecting front and back portions of the waist portion, the crotch portion comprising an absorbent core for absorbing body exudates and a liquid-permeable topsheet which in use faces a user's crotch, the topsheet covering the absorbent core, the method comprising the steps of: composing the articles from a plurality of fabrics which define the colours of inside and outside surfaces of the articles, the liquid-permeable topsheet being made from one of said fabrics, the fabrics having colours which are chosen such that: (i) at least the outside surfaces of all of said plurality of articles have, in the CIE $L*a*b*$ colour space, $L*$ values less than 80 and mutual colour differences $\Delta E*ab$ less than 10; (ii) for all of said plurality of articles, a surrounding zone of the inside surface, which is a part on the topsheet which at least partly surrounds an absorption zone where the absorbent core is located underneath, also has an $L*$ value less than 80 and a mutual colour difference $\Delta E*ab$ less than 10 with the outside surface of the respective article; and (iii) for all of said plurality of articles, the absorption zone has an $L*$ value less than 90 and a colour difference $\Delta E*ab$ more than 5 with respect to the surrounding zone and/or the outside surface of the respective article.

So, in the method according to the disclosure, preferably the outside surfaces and the surrounding zones on the inside of the articles all have substantially the same colour, with an $L*$ value less than 80, while the absorption zone is of a different colour. This can be achieved by using fabrics of the same or substantially the same colour, except for certain parts like e.g. the absorbent core. An advantage of using the same colour is that any colour contamination from one fabric layer to another is not noticeable on the finished articles.

BRIEF DESCRIPTION OF THE DRAWINGS

The present disclosure will be discussed in more detail below, with reference to the attached drawings.

FIG. 1 is a perspective view of an embodiment of an absorbent pant article.

FIG. 2 is a simplified plan view of the absorbent pant article in its flat, non-contracted state.

FIG. 3 is a cross section according to the line III-III in FIG. 2.

FIG. 4 is a cross section through an elastic laminate according to the invention.

FIG. 5 is a schematic cross section according to the line V-V in FIG. 2.

FIG. 6 is a schematic cross section similar to FIG. 5 but illustrating another embodiment.

FIG. 7 is a plan view similar to FIG. 2 but showing a further embodiment of an absorbent pant article.

FIGS. 8-13 show a second set of embodiments according to the present disclosure.

FIG. 9 shows a top view of the absorbent article;

FIG. 10 shows a schematic illustration of a manufacturing process for an absorbent article according to the disclosure;

FIG. 12 shows a cross-sectional view of a crotch section of said absorbent article;

DESCRIPTION OF EMBODIMENTS

Figure 1:
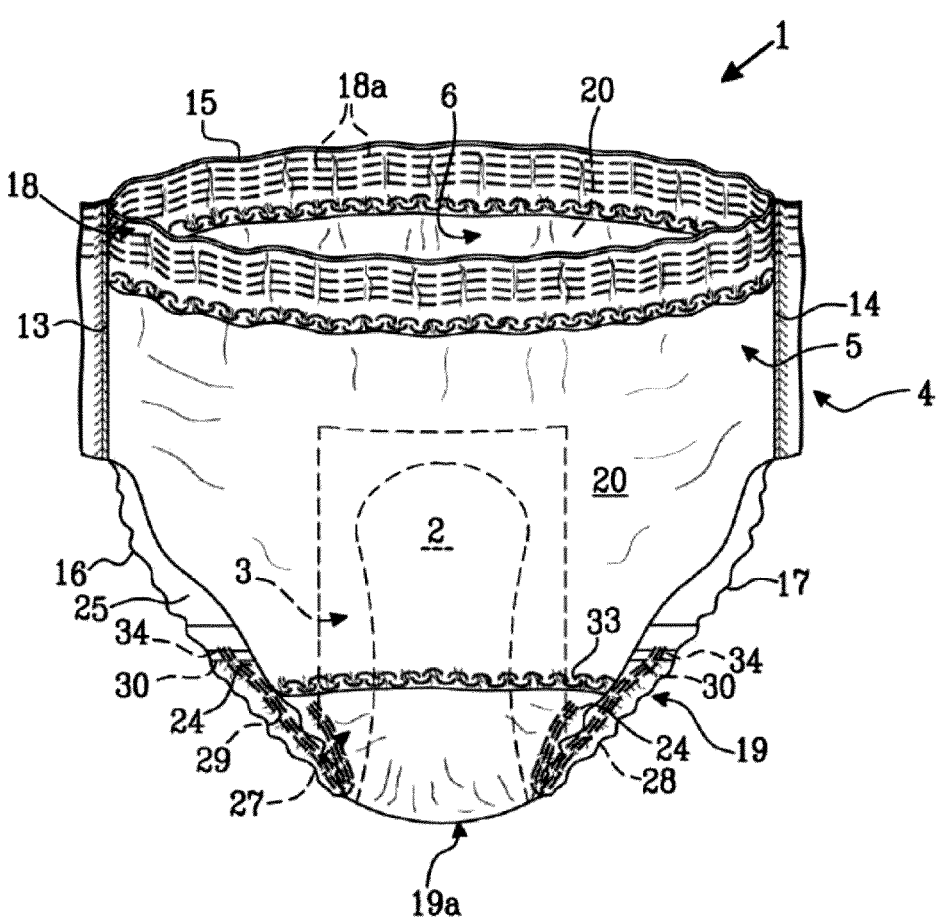
FIGS. 1-7 show a first set of embodiments according to the present disclosure.

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure.

Furthermore, the terms first, second, third and the like in the description and in the claims, are used for distinguishing between similar elements and not necessarily for describing a sequential or chronological order. The terms are interchangeable under appropriate circumstances and the embodiments of the disclosure can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the disclosure described herein can operate in other orientations than described or illustrated herein.

Furthermore, the various embodiments, although referred to as "preferred" are to be construed as exemplary manners in which the disclosure may be implemented rather than as limiting the scope of the disclosure.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present disclosure, the only enumerated components of the device are A and B, and further the claim should be interpreted as including equivalents of those components.

The embodiments described herein mainly refer to disposable absorbent articles, which means articles that are not intended to be laundered or otherwise restored or reused as an absorbent article after use. The embodiments are pant-type absorbent articles such as a pant diapers, sanitary pants and incontinence pants and especially pant-type absorbent articles intended for adult wearers.

Figure 14A:
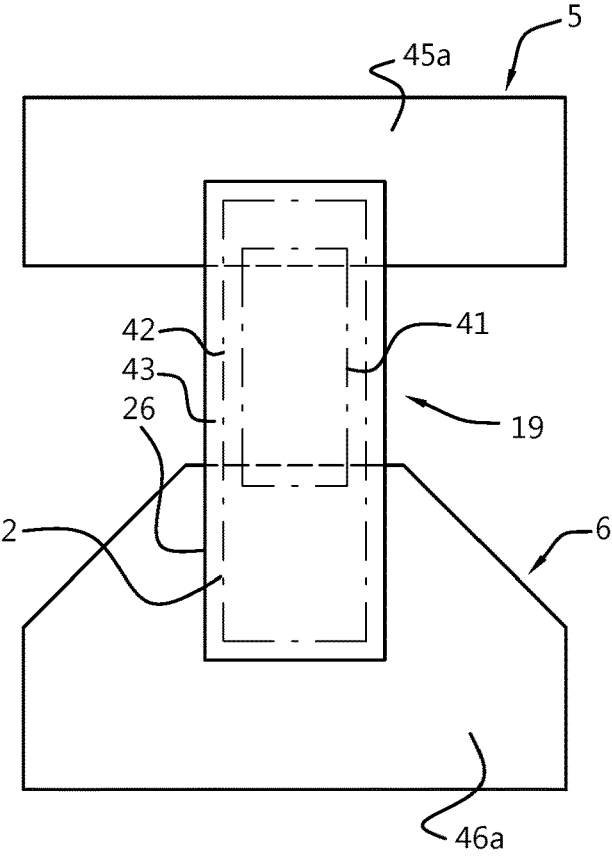
FIGS. 14A and 14B schematically show the inside and outside of articles according to FIGS. 1-13.
Figure 14B:
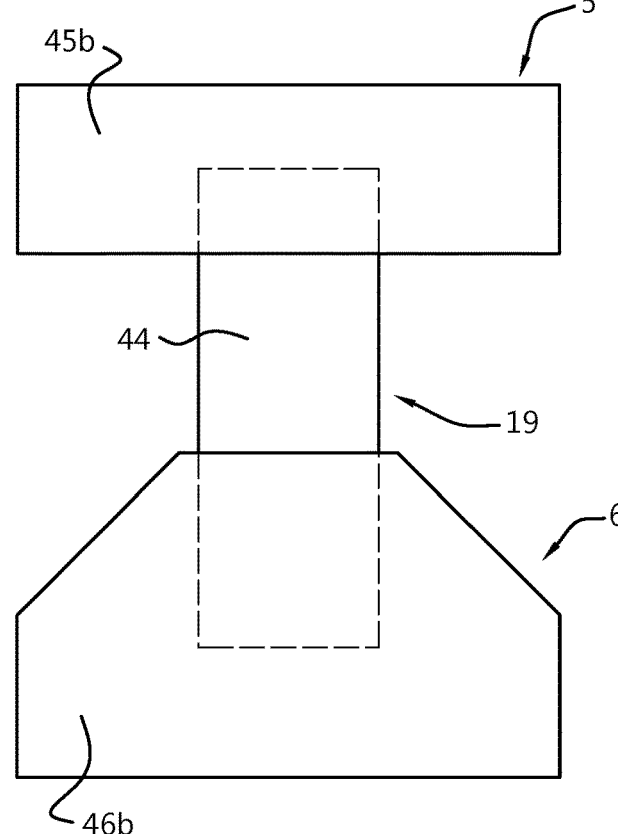

A first set of embodiments of absorbent articles according to the present disclosure will be described with reference to FIGS. 1-7, in particular elastic film laminate-type pant articles. FIGS. 14a and 14b schematically show the inside and outside of such articles.

Such elastic film laminate-type pant articles comprise waist and crotch portions which include a pant-shaped chassis and an absorbent core component integrated with the chassis. They are intended to fit comfortably and snugly about the wearer. It is further desirable that the articles are capable of being pulled up and down over the hips of the wearer to allow the wearer or caregiver to easily put on and remove the article when it has been soiled. Thereto, portions of the chassis are composed of an elastic laminate comprising first and second layers of fibrous material and an elastic film layer located there between. Such articles are for example known from WO 2005/122985, WO 2007/133127 and WO 2016/068764. Chassis composed of elastic laminates of this type are relatively smooth with less wrinkles as compared to laminates comprising elastic strands sandwiched between fibrous materials, as disclosed in for example 2003/0028166 and US 2009/0275911.

Figure 2:
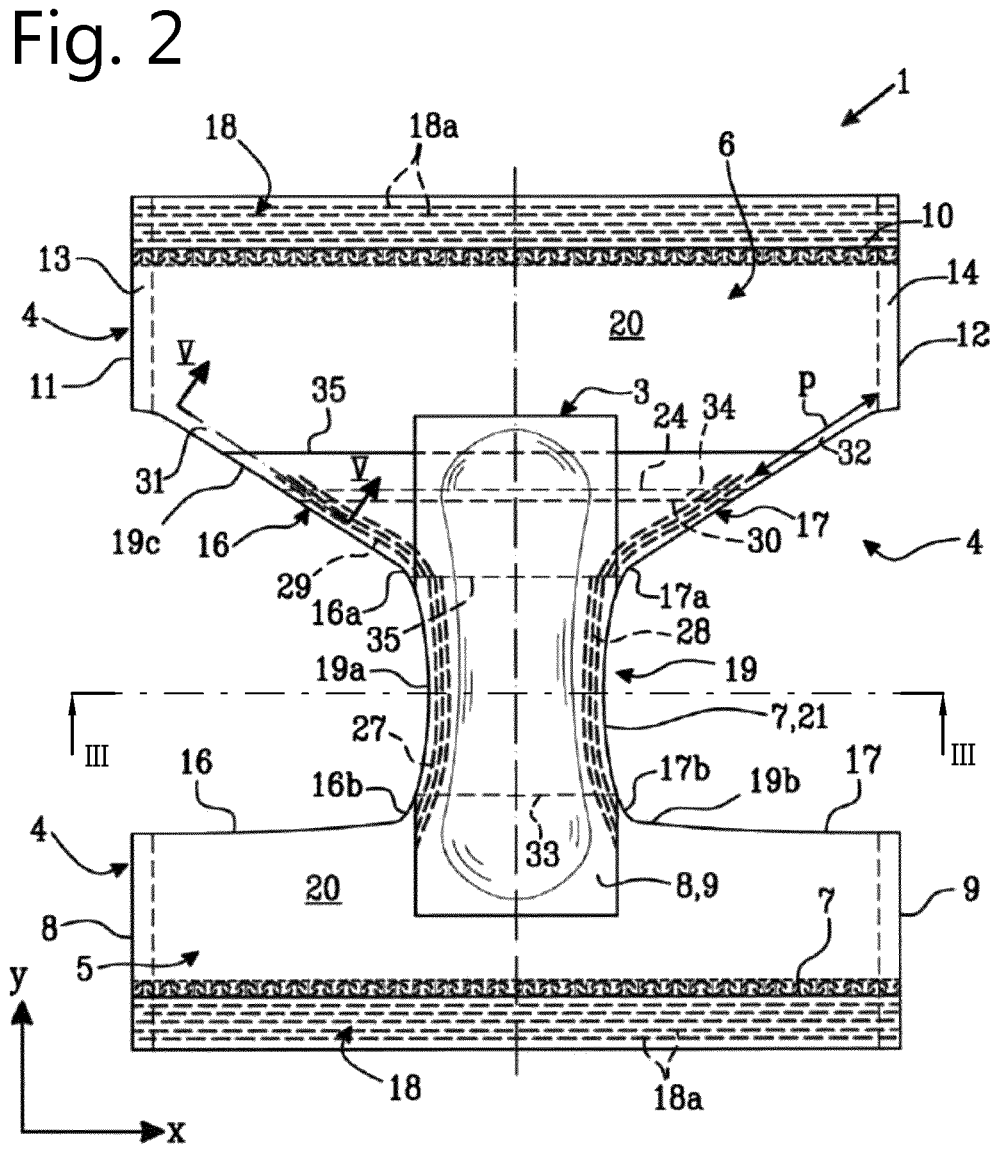
Figure 3:
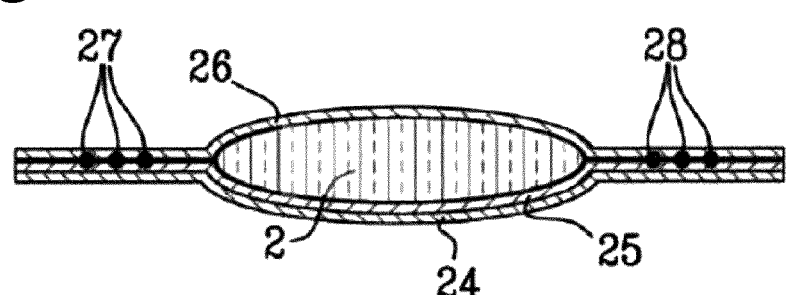
Figure 4:
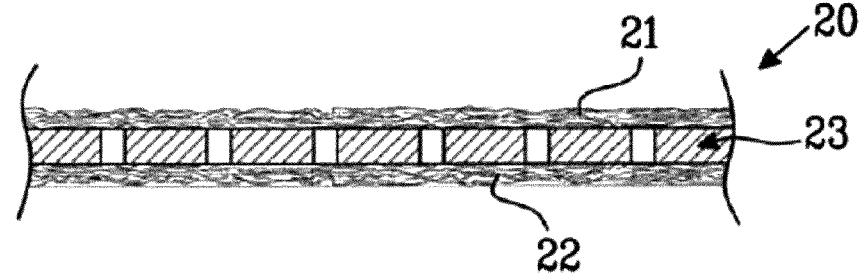
Figure 5:
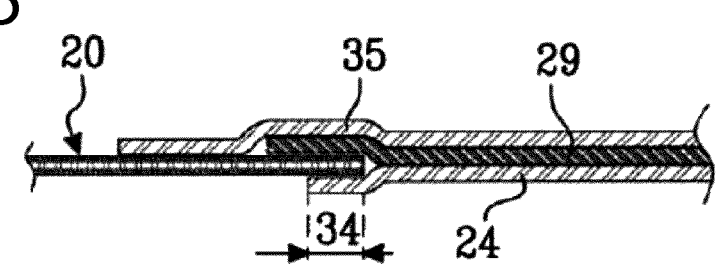

The elastic film laminate-type absorbent article 1 disclosed in FIGS. 1 and 2 is intended to enclose the lower part of the wearer's trunk like a pair of underwear. The article 1 comprises a core region 3 with an absorbent core 2, which defines the "absorption zone". The article further comprises a chassis 4. The article has a longitudinal (y) and a transverse direction (x). The chassis 4 comprises a front portion 5 and a back portion 6, together forming a waist portion which in use surrounds the wearer's waist. The front portion 5 has a front transverse edge 7 and first and second longitudinal side edges 8 and 9. The back portion 6 has a back transverse end edge 10 and first and second longitudinal side edges 11 and 12. The front and back portions 5 and 6 are joined to each other along their respective first and second longitudinal side edges by ultrasonic welds, glue strings or the like to form first and second side seams 13 and 14 and to define a waist-opening 15.

The chassis may further comprise an elastic waist band 18 comprising elongated elastic members 18a. The elastic waist band 18 is secured to the transverse end edges 7 and 10 of the front and back portions 5 and 6. The elastic waist band portions 18 are joined to each other along said side seams 13 and 14. Alternatively, the elastic waist band may comprises first and second plies of substantially non-elastic nonwoven material that is elasticized by one or more elongate elastic members, such as elastic threads or bands. The first and second plies can be formed from a single layer of material that is folded over onto itself or can be made from two separate strips of material. A further option is to create the portion from one or more non-elastic nonwoven layers that are also parts of the front and back panels and form continuous extensions thereof. It is also conceivable to form an elastic waist feature by double-folding portions along the waist edges of the elastic front and back panels and optionally supplementing the folded portions by additional elastic elements.

The article 1 further comprises a connecting portion 19 located between the front portion 5 and the back portion 6 in the longitudinal direction of the article. The connecting portion 19 defines a crotch portion 19a and first and second leg openings 16 and 17. The boundary between the connecting portion 19 and the front and back portions 5 and 6 is along a transverse line extending between the lower edges of the side seams 13 and 14 adjacent the leg openings 16 and 17. The entire leg openings 16 and 17 are thus located in the connecting portion 19. The core region 3 is located in the connecting portion 19 and may extend into the front and/or back portions 5 and 6.

In the pant article shown in FIG. 2 the connecting portion 19 has defined points in the leg openings 16 and 17 where the width of the connecting portion 19 increases abruptly. These points are denoted 16a, 16b, 17a, 17b. In the pant article shown in FIG. 7 the leg openings 16 and 17 have a more or less continuous curvature with no such abrupt change of the radius of curvature.

A backsheet material 25 underlies the absorbent core 2 and adjacent areas immediately outside the absorbent core 2. The backsheet is preferably liquid-impervious. The area covered by the backsheet 25 is defined as the core region 3. A liquid-pervious topsheet material 26 is arranged on the wearer-facing side of the absorbent core 2, so that the absorbent core 2 is enclosed between the backsheet material 25 and the topsheet material 26. The absorbent core 2, the backsheet 25 and the topsheet 26 form an absorbent assembly.

The preferably liquid-impervious materials used for the backsheet 25 may be a thin plastic film, e.g. a polyethylene or polypropylene film, a nonwoven material coated with a liquid impervious material, a hydrophobic nonwoven material which resists liquid penetration or a laminate comprising plastic films and nonwoven materials. The backsheet 25 may be breathable so as to allow vapour to escape from the absorbent core, while still preventing liquids from passing therethrough. Examples of breathable backsheet materials are porous polymeric films, nonwoven laminates from spunbond and meltblown layers, laminates from porous polymeric films and nonwovens.

The liquid-pervious materials used for the topsheet 26 may be a nonwoven material, e.g. spunbond, meltblown, carded, hydroentangled, wetlaid etc. Suitable nonwoven materials can be composed of manmade fibres, such as polyester, polyethylene, polypropylene, viscose etc. or natural fibers, such as woodpulp or cotton fibres, or from a mixture of natural and manmade fibres. Further examples of topsheet materials are porous foams, apertured plastic films etc.

Preferably, coloured non-woven material is used for the topsheet 26, preferably having the same or substantially the same colour as at least the fabric layers of the article which define the colour of the outside of the article. The absorption zone, i.e. where the core is located, is preferably of a lighter colour as a result of the core, which may be entirely in relatively light colours, shining through the non-woven material of the topsheet 26.

Preferably, coloured material is also used for the backsheet 25, preferably the same colour as the topsheet 26.

The absorbent core 2 can be of any conventional kind. Examples of common absorbent materials used in absorbent cores are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core.

It is conventional in absorbent articles to have an absorbent core 2 comprising layers of different properties with respect to liquid receiving capacity, liquid distribution capacity and storage capacity. The thin absorbent bodies, which are common in for example baby diapers and incontinence articles, often comprise a compressed mixed or layered structure of cellulosic fluff pulp and superabsorbent polymers. The size and absorbent capacity of the absorbent core may be varied to be suited for different uses such as for infants or for adult incontinent persons.

The absorbent core 2 may further include an acquisition distribution layer (not shown) placed on top of the primary absorbent body and which is adapted to quickly receive and temporarily store discharged liquid before it is absorbed by the primary absorbent core. Such acquisition distribution layers are well known in the art and may be composed of porous fibrous waddings or foam materials.

The layers or fabrics forming at least the top side of the core, e.g. the acquisition layer, are preferably of lighter colours, preferably at least lighter than the topsheet 26, for example L* values above 90, for example white or substantially white.

At least part of or the entire front and back portions 5 and 6 may be composed of an elastic laminate material 20. By the term "elastic" is meant that the material is capable of being extended under a force and then is capable of contracting back to or towards its initial length once the force is removed. The elastic laminate 20 used in the pant-type absorbent article may have an elasticity in the x-direction of the article of at least 30%, preferably at least 50%, more preferably at least 70%. The elastic laminate material 20 may also be elastic in the y-direction of the article. However the elasticity in the y-direction is preferably lower than in the x-direction.

Preferably the elastic laminate material 20 is also elastic in the y-direction of the article. However the elasticity in the y-direction is preferably lower than in the x-direction.

The term "non-elastic" refers to any material that does not fall within the definition of an "elastic" material given above.

The elastic laminate 20 may cover the entire article, including the core region 3 and the entire chassis region 4. However, in a preferred embodiment a part of the connecting portion 19 of the article is free from the elastic laminate material 20. The part of the connecting portion 19 that is free from the elastic laminate 20 includes the narrow part which is referred to as the crotch region 19*a*. The waist band 18 may or may not be free from the elastic laminate material 20. The waist band may comprise a nonwoven material that is elasticized by elongated elastic members 18*a*, such as elastic threads, contractably affixed between material layers, such as nonwoven materials. Ultrasonic welds, glue strings or the like, join the elastic laminate 20 to the elastic waist band 18.

The elastic laminate 20 preferably extends continuously laterally across the width of the front portion 5 between the first and second side edges 8 and 9 as well as continuously laterally across the width of the back portion 6 between the first and second side edges 11, 12. The elastic laminate 20 also extends continuously laterally across the width of the connecting portion 19 between the leg openings 16 and 17 in those parts of the connecting portion 19 where the elastic laminate 20 is present.

The elastic laminate 20 is composed of inner and outer layers of fibrous material 21 and 22, which form inner and outer fabrics of the article, and an elastic film 23 located between said fibrous layers. The elastic laminate 20 may also comprise one or more additional fibrous layers laminated to one or both of the first and second fibrous layers. Such additional fibrous layers may be present only in parts of the elastic laminate 20. Thus the elastic laminate 20 need not be identical all over its area, but may comprise different layers in different areas.

The inner and outer layers 21, 22 of the elastic laminate form portions of the inside and outside surface of the article. The material of these layers is preferably coloured, preferably has the same colour as the topsheet 26.

It is advantageous that the inner and outer fibrous layers are chosen so that they, in combination with the inner elastic film layer, give the material high resistance to puncture. They also provide a soft and cloth-like feel to the laminate. Examples of suitable materials are carded webs and spunbond materials. The basis weight of the fibrous material layers should be between 8 and 35 g/m2, preferably between 10 and 25 g/m2, more preferably between 12 and 25 g/m2. Examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the nonwoven layer, and through this, give the nonwoven material a higher elongation at maximum load. A mixture of polyethylene and polypropylene polymers has proved to provide good results in this respect. A mixture of fibers of different polymers is also possible.

At least one of the fibrous layers of the elastic laminate may be a creped nonwoven material. The creped nonwoven will increase the puncture resistance of the laminate puncture resistant and allow it to be subjected to the pulling and stretching forces that occur when putting on and taking off the pant article without breaking and tearing.

The middle layer is preferably an apertured elastic film 23 having a basis weight between 20 and 80 g/m2, preferably between 20 and 60 g/m2. The film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film of PE-SEBS-PE.

It is further preferred that the elastic laminate 10 has a breathability (Water Vapour Transmission Rate) according to ASTM E96-00 Procedure D of at least 1500 g/m2 24 h, preferably at least 3000 g/m2 24 h.

The open area of the elastic film layer is preferably at least 5%, more preferably at least 8%. The open area is measured by image analysis methods and is defined as the sum of the hole area divided by the total area of the film sample.

In the following, methods for manufacturing elastic laminates 20 are described. In accordance with the present disclosure, coloured materials are used for the inner and/or outer fibrous layers of the laminate, in order to achieve a finished article with coloured inner and/or outer fabrics. Preferably, the same colour is used for both the inner and outer fibrous layers 21, 22.

One method for manufacturing an elastic laminate is described in WO 03/047488, wherein one spunbond layer is applied to the film, said film being in a tacky state and will thus bond to the spunbond layer, while the other spunbond layer is adhesively laminated to the film layer, using for example a pressure sensitive hot melt adhesive. Alternatively the laminate is manufactured according to a modified version of this known method, wherein the modification involves that the laminate is incrementally stretched (through intermeshing gears, IMG), to a point below the elongation at peak load of at least one of the non-elastic nonwoven layers to retain some strength for at least one of the nonwoven layers. The other layer may also be stretched to a point below its elongation at peak load, or to a point at which it will tear during stretching.

The method disclosed in WO 03/047488 involves stretching of the laminate above the point of failure of the fibrous material, so that the non-elastic layers break completely. Therefore, as described in WO 03/047488, the elongation of the laminate is not limited by the stretch modulus of the non-elastic material.

According to a modified method at least one, preferably both fibrous layers, which are bonded to the elastic film are not, in contrast to the method described in WO 03/047488, completely torn upon manufacture of a laminate. Selection of fibrous materials which have an elongation at maximum load greater than the elasticity of the elastic laminate allows the elastic film to stretch without being hindered by the fibrous layers. Such a selection also ensures that the fibrous layers contribute to the puncture resistance of the laminate, as they are not completely torn or broken during manufacture. Preferably the fibrous layers, or at least one of the fibrous layers has an elongation at maximum load that is at least 10% higher than the elasticity of the laminate. This is described in more detail in WO 2005/122985.

In an alternative embodiment the laminate 20 is manufactured by feeding a first fibrous layer in the form of a nonwoven web into a bonding nip and extruding a molten elastic film-forming polymer through a die into the nip. The first fibrous layer and the elastic film form a first laminate. In a second lamination step the film side of the first laminate is coated or sprayed with adhesive and is subsequently passed through a second bonding nip together with a second fibrous layer to form the laminate 20. The laminate is subsequently activated by subjecting it to incremental stretching by passing it through intermeshing gears, IMG.

In a further embodiment the inner layer 21 of fibrous material and the elastic film layer 23 form parts of a first elastic laminate that has been rendered elastic by incremental stretching and partial tearing of the inner layer of fibrous material and in which the first elastic laminate has been bonded to the outer layer 22 of fibrous material while in a stretched state. The resulting laminate will then be elastically stretchable.

In a still further embodiment the inner and outer layers 21, 22 of fibrous material have been bonded to the elastic film layer 23 while this is in a stretched state, so called stretch-bonding. The resulting laminate will be elastically stretchable.

The elastic laminate material 20 is preferably arranged as an outside coversheet material as well as inner coversheet material over at least part of the front portion 5, back portion 6 and connecting portion 19 of the chassis 4. The elastic laminate material may constitute the sole component of the chassis 4 in at least 20%, preferably at least 25%, more preferably at least 30% and most preferably at least 40% of the total surface area of the article, as seen in a flat state according to FIGS. 2 and 7.

No additional elasticized side panels joining the front and back portions 5 and 6 are needed when using the elastic laminate material 20.

The elastic laminate 20 and the backsheet 25 overlap in the outer parts of the core region 3, wherein the elastic laminate 20 is arranged on the garment facing side of the backsheet 25.

The absorbent assembly comprising the liquid impervious backsheet material 25, the liquid pervious topsheet material 26 and the absorbent core 2 enclosed therebetween, all of which components are described above, may be joined to the elastic laminate 20 of the front, back and/or connecting portions 5, 6 and 19 while this is held in a selectively stretched condition, so that gathers are present in the absorbent assembly at those points where it is joined to the front, back and/or connecting portions 5, 6 and 19.

As mentioned above the elastic laminate 20 may be absent in a substantial part of the connecting portion 19 of the article. A crotch panel material 24 may underlie at least part of the absorbent assembly on the garment-side thereof. The crotch panel material 24 may be of a non-elastic web material, although elastic materials may also be used. In case an elastic material is used as crotch panel material 24 it should be less elastic than the elastic laminate 20. Suitably, the crotch panel material is a nonwoven material. The crotch panel material 24 is joined to the elastic laminate 20 along seams 33 and 34.

Preferably the elastic laminate 20 is held in a stretched condition when joined to the non-elastic crotch panel material 24, wherein gathers are formed in the crotch panel material when the stretching force is released.

Figure 6:
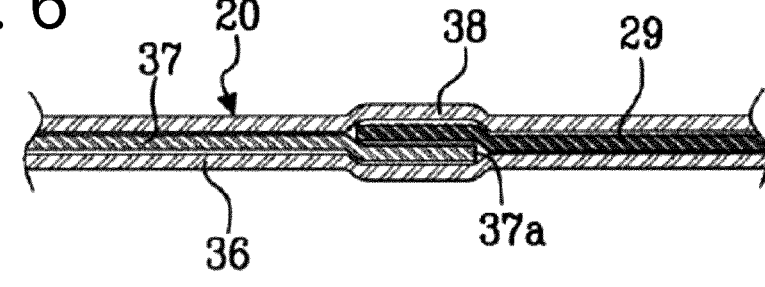

In an alternative embodiment illustrated in FIG. 6 there is no separate crotch panel material 24 joined to the elastic laminate 20 along seams, but the elastic laminate 20 is defined by an elastic film 37 laminated to only part of inner and outer nonwoven layers 36 and 38, wherein the transverse edge 37a of the elastic film 37 forms the boundary between the elastic laminate and the non-elastic crotch panel material. This will be described more in detail below.

Elongated leg elastic members such as elastic threads extend along part of the leg openings 16 and 17 in the connecting portion 19. In the embodiment disclosed in FIG. 2 the leg opening elastic members are divided in first elastic members 27 and 28 extending along the respective longitudinal edges of the crotch region 19a and second elastic members 29 and 30 extending along the edges of part of the leg openings 16 and 17 outside the area of the crotch region 19a. The area of the connecting portion 19 outside the crotch region 19a and that faces the front portion 5 is defined as the front part 19b of the connecting portion 19 and the area of the connecting portion 19 outside the crotch region 19a and that faces the back portion 6 is defined as the back part 19c of the connecting portion 19.

The first elastic members 27 and 28, which extend along the narrow part of the connecting portion 19 referred to as crotch region 19a provide for a sealing effect in the crotch part preventing leakage of body fluid.

Figure 7:
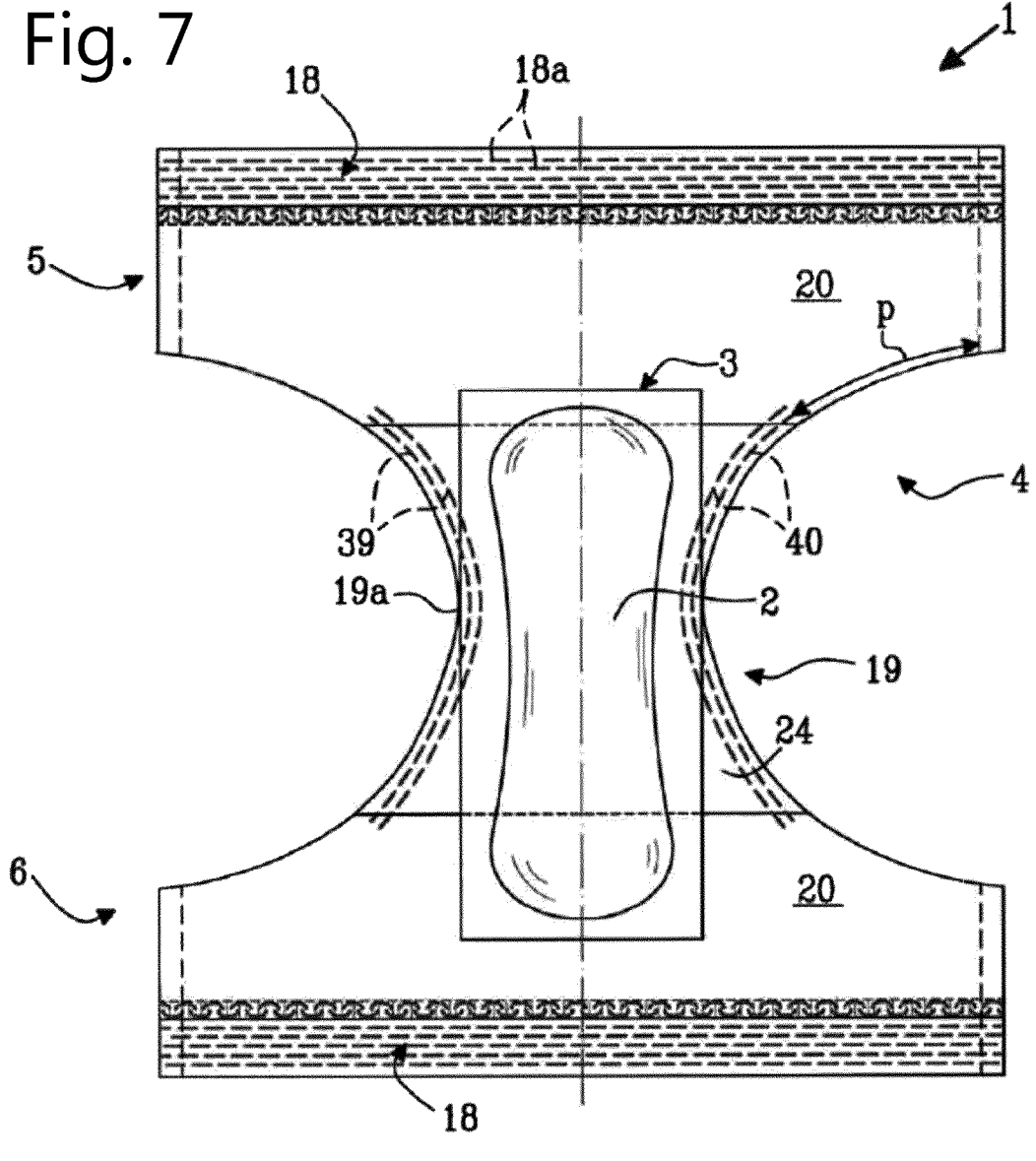

In the embodiment disclosed in FIG. 7 leg elastic members 39, 40 extend continuously along part of the leg openings 16 including the crotch region 19a.

In the embodiments shown in FIGS. 1-7 the elastic laminate material 20 covers more or less the entire front portion 5, the entire back portion 6 and part of the connecting portion 19, i.e. part of the leg opening area. In the embodiment disclosed in FIG. 2 the elastic laminate material 20 covers the entire front part 19*b* of the connecting portion 19 but only part of the back part 19*c* of the connecting portion 19. The part of the leg opening area in the connecting portion 19 covered by the elastic laminate 20 is elastic also in the absence of additional leg elastics.

In the embodiment shown in FIG. 2 the second elastic members 29 and 30 extend from an area adjacent the point 16*a*, 17*a* in the connecting portion 19 where the first elastic members 27 and 28 terminate and where the width of the article increases abruptly. The second elastic members 29 and 30 are only arranged in the back part 19*c* of the connecting portion 19 that is facing the back portion 6, while no second elastic members 29 and 30 are arranged in the front part 19*b* of the connecting portion 19.

The second elastic members 29 and 30 do not extend all the way to the side seams 13 and 14 but terminate in the leg openings 16 and 17 at a distance from the respective side seam 13 and 14 thus leaving an area 31 and 32 corresponding to a peripheral length p of at least 50 mm, preferably at least 75 mm and more preferably at least 100 mm along the respective leg opening 16 and 17 where the leg elastic members 29 and 30 are absent. The peripheral length p is measured along the periphery of the respective leg opening 16 and 17 and is measured to the inner edge of the respective side seam 13 and 14. When more than one elongated elastic member is present in the leg elastics (which normally is the case) the peripheral length (p) is measured from the elastic member where said length is shortest. The length p is measured in a flat, non-contracted state of the article as illustrated in FIG. 2. Said flat, non-contracted state of the article corresponds to the degree of stretching the elastic laminate has during the production process, when attaching non-elastic material components thereto.

The connecting portion 19 in the area adjacent the leg openings 16 and 17 where the leg elastic members 29 and 30 are absent is composed of the elastic laminate material 20 along at least 80%, preferably at least 85% and more preferably at least 90% of the peripheral length p.

As described above a crotch panel material 24 is arranged in the crotch region 19*a* of the connecting portion 19 and is joined to the elastic laminate 20 of the connecting portion 19. The crotch panel material 24 is preferably non-elastic. The leg elastic members 27-30 extend along at least part of the leg openings 16 and 17 in the connecting portion 19 defined by the crotch panel material 24. The leg elastic members 27-30 preferably extends along at least 90% of the part of the leg openings 16 and 17 which are located in said crotch panel material 24, wherein said length is measured along the periphery of the respective leg opening.

The leg elastic members 27-30 may extend a certain distance into the part of the leg openings 17 and 18 defined by the elastic laminate 20, or they may end in the boundary between the elastic laminate 20 and non-elastic crotch panel material 24, such as in a seam 34 joining the elastic laminate 20 to the crotch panel material 24. Preferably the leg elastic members 27-30 overlaps the elastic laminate 20 not more than 20 mm and more preferably not more than 15 mm.

A cover strip 35, preferably a nonwoven material, may be laminated on the wearer-facing side of the article covering the leg elastic members 29 and 30. The cover strip 35 preferably extends the entire width of the article. The cover strip 35 forms part of the elastic laminate 20 so that the part of the elastic laminate 20 to which the cover strip 35 is laminated maintains at least a substantial part of its elastic properties.

The leg elastics 29 and 30 retract the web material to which they are attached causing wrinkles, which can be seen through the clothing. The arrangement of having leg elastics 29 and 30 that do not extend all the way to the side seams 13 and 14 results in smoother leg openings with less wrinkles and a more discrete article. Since at least a major part of the leg openings where the leg elastics are absent is composed of the elastic web material 20 there will be a certain sealing effect also in the area where the leg elastics are absent.

In an alternative embodiment illustrated in FIG. 6 there is no separate crotch panel material 24. Instead a base layer nonwoven 36 extends over the front, back and crotch portions 5, 6 and 19 and forms an outer coversheet material thereof. An elastic film 37 is laminated to the base layer nonwoven 36 in the front and back portions 5 and 6. A cover layer nonwoven 38 is laminated to the opposite side of the elastic film 37, and forms an inner coversheet of the article. The base layer nonwoven 36, the elastic film 37 and the cover layer nonwoven 38 forms an elastic laminate 20 as described above. The base layer nonwoven 36 and the cover layer nonwoven 38 are preferably per se non-elastic, wherein the article is elastic only in those parts where elastic film 37 is present. The base layer nonwoven 36 and the cover layer nonwoven 38 form the crotch panel material in this embodiment.

The elastic film 37 extends preferably transversely across the width of the front portion 5 between the first and second side edges 8, 9, transversely across the width of the back portion 6 between the first and second side edges 11, 12 and transversely across part of the connecting portion 19 between the leg openings 16 and 17. The elastic film 37 has a transverse edge 37*a* at its end facing the crotch region 19*a* of the connecting portion 19.

Elongated leg elastic members 29 and 30 are attached between the base layer nonwoven 36 and the cover layer nonwoven 38 along part of the respective leg opening 16 and 17 at least in areas where the elastic film 37 is absent, in a corresponding manner as disclosed with respect to the embodiment described above. Preferably the leg elastic members 29 and 30 extend at least along 80%, preferably at least along 85% and more preferably along at least 90% of the part of leg openings 16 and 17 located in said area where the elastic film 37 is absent, wherein said length is measured as the peripheral length p along the respective leg opening. Preferably the leg elastic members 29 and 30 overlap the elastic film 37 not more than 20 mm and more preferably not more than 15 mm.

In the embodiment disclosed in FIG. 7 the leg openings 16 and 17 have a different curvature than in the embodiment disclosed in FIG. 2 and leg elastic members 39 and 40 extend continuously along part of the leg openings 16 and 17 including the crotch part 19*b* of the connecting portion 19. In other words this embodiment is similar to the ones described above.

A second set of embodiments of absorbent articles according to the present disclosure will be described with reference to FIGS. 8-13, in particular threaded type pant articles. FIGS. 14*a* and 14*b* schematically show the inside and outside of such articles.

Figures 8A, 8B:
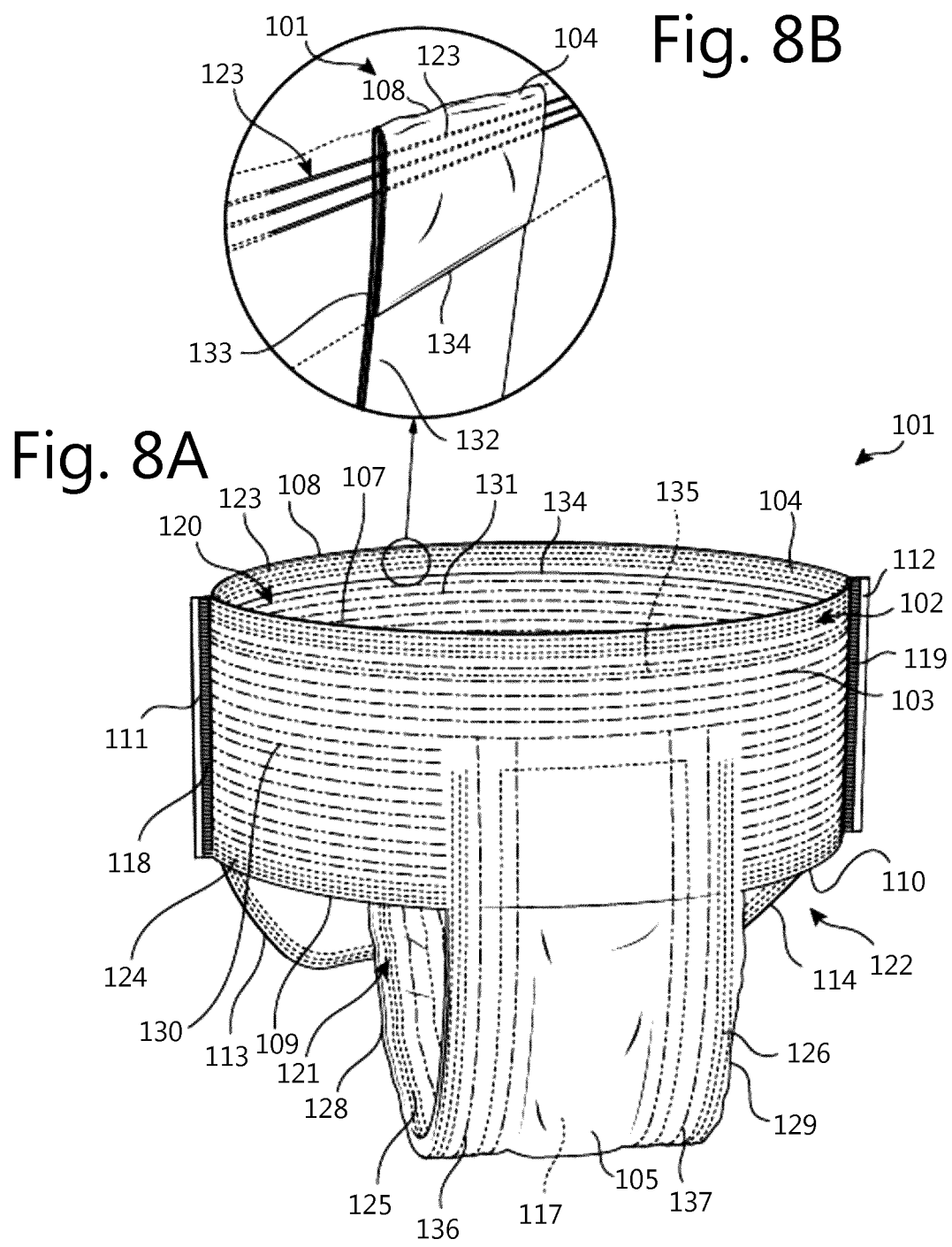
FIG. 8A shows a perspective front view of the absorbent article according to the disclosure.
FIG. 8B is a perspective view of an enlarged section of a waist edge forming part of the absorbent article.
Figure 9:
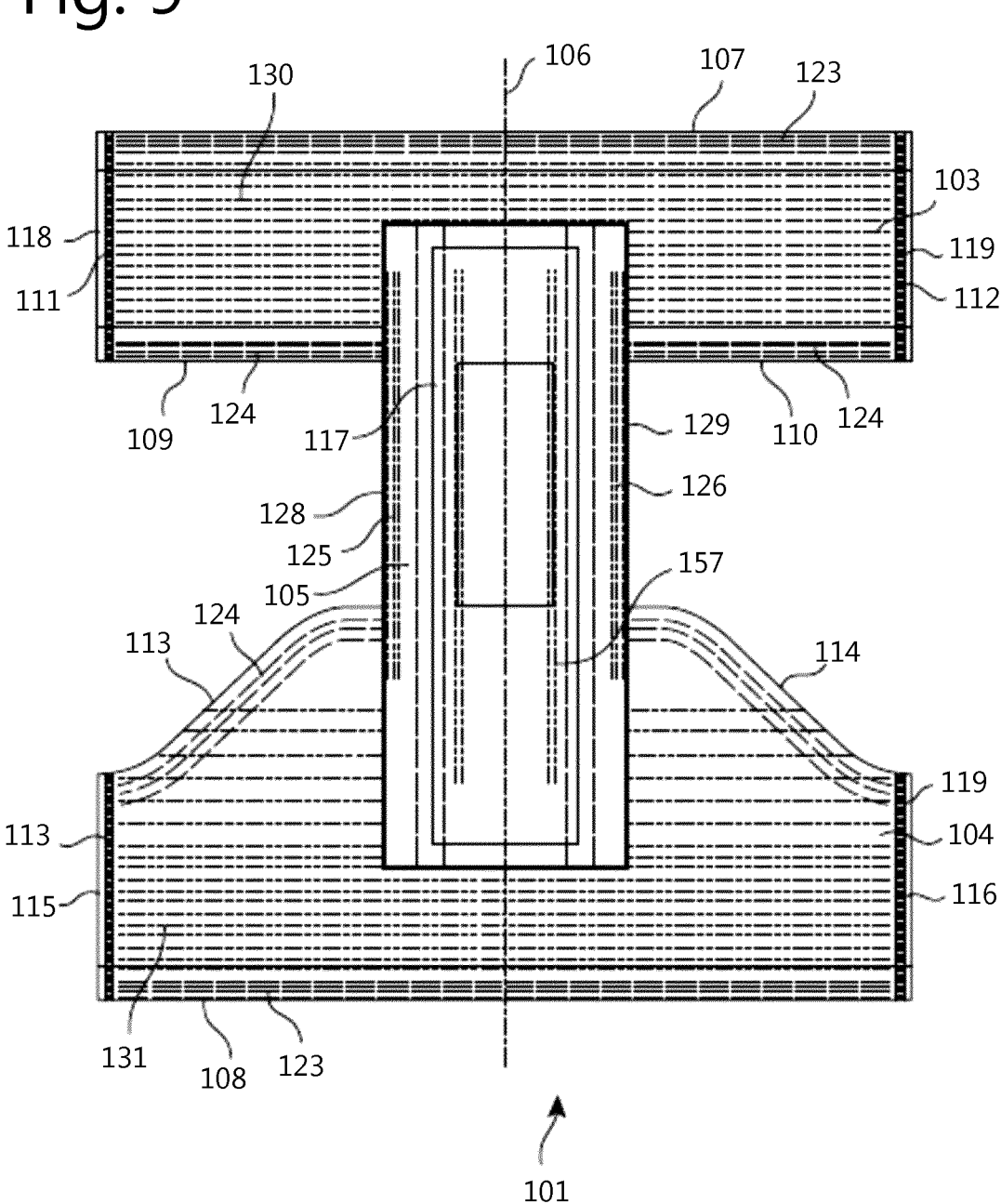

With reference to FIG. 8*a* of the drawings, there is shown an embodiment of a disposable pant-type absorbent article 101 illustrated in an assembled and ready-to-use state. The same absorbent article 101 is also shown in FIG. 9, but in a condition in which it is laid out flat and as viewed from above in order to show its main components. Furthermore, FIG. 8b is a perspective view of an enlarged section of a part of the absorbent article 101, as will be described in greater detail below.

The article 101 shown in FIGS. 8-9 is not intended to describe a specific male or female model, but is used to describe the general principles of an article which can be either suited for male or female users. However, FIGS. 13a and 13b, which will be described in detail below, and indicate the difference between male and female articles.

With reference to FIG. 8a and FIG. 9, the pant-type absorbent article 101 is for example in the form of a pant diaper, a sanitary pant or an incontinence pant adapted for use by a baby, child or adult, male or female user. The pant-type absorbent article 101 according to FIG. 8 comprises a single-piece chassis 102 having a front portion 103, a back portion 104, a crotch portion 105 connecting the front and back portions 103, 104, and a centre line 106 (see FIG. 9) in the longitudinal direction of the article. The absorbent article 101 has a longitudinal direction, a transverse direction and a thickness direction.

The front portion 103 has a waist edge 107, a pair of leg edges 109, 110 and a pair of side edges 111, 112. Furthermore, the back portion 104 has a waist edge 108, a pair of leg edges 113, 114 and a pair of side edges 115, 116.

As mentioned above, the absorbent article 101 comprises a crotch portion 105, which comprises an absorbent body 117 located mainly in said crotch portion 115. The absorbent body 117 may be manufactured separately from the chassis 102 and inserted and fastened to the chassis 102 at a suitable manufacturing step. This process will be described in greater detail below.

The side edges 111, 112 of the front portion 103 are attached to the opposite side edges 115, 116 of the back portion 104 by means of permanent or re-closable side connections 118, 119 such as side seams, hook and loop fasteners, adhesive fasteners, or the like, in order to at least partly define a waist opening 120 and a pair of leg openings 121, 122.

A first elastic element in the form of an elastic waist component 123 is fastened to the chassis 102 at least partly along the waist edges 107, 108 forming part of the front portion 103 and the back portion 104. The purpose of the elastic waist component 123 is to provide the absorbent article 101 with a good fit around the waist of the user wearing the article. The elastic waist component 123 is fastened relatively close to the waist edges 107, 108, around the waist opening 120.

Furthermore, a second elastic element in the form of an elastic leg component 124 is fastened to the chassis 102 at least partly along the leg edges 109, 110 of the front portion 102 for the purpose of providing the absorbent article 101 with a good fitting around the legs of the user wearing the article. The elastic leg component 124 is fastened relatively close to the leg edges 109, 110.

As shown in particular in FIG. 9, the elastic leg component 124 forms a straight line in the front portion 103 and has a curved configuration in the back portion 104.

Furthermore, a first absorbent body elastic 125 and a second absorbent body elastic 126 are arranged along the crotch portion 105. The first absorbent body elastic 125 is arranged along a first crotch edge 128 whereas the second absorbent body elastic 126 is arranged along a second crotch edge 129. In particular, the first absorbent body elastic 125 and the second absorbent body elastic 126 are arranged relatively close to the longitudinal crotch edges 128, 129. In a similar manner, the elastic waist component 123 and the elastic leg component 124 are also arranged relatively close to the waist edges 107, 108 and the leg edges 109, 110, respectively, as shown in FIG. 8 and FIG. 9.

If the elastic leg component 124 and the elastic waist component 123 are fastened at a location close to the leg and waist edges 107, 108, 109, 110, respectively, less non-elasticised web material is available at the leg and waist edges such that less frills is created along said edges. This is an advantage, since a large amount of material at the leg edges may be perceived as uncomfortable by a user and may give the user an impression that the article is not similar to conventional underwear.

Having the elastic leg feature 124 positioned closer to the leg edge 109, 110 may also result in an absorbent article 101 having an improved fit which corresponds to the shape of the legs of the user. It is thus desirable to provide an elasticised leg edge 109, 110 of the front and back portion 103, 104 that has a more cuff like appearance with less frills, thereby providing the absorbent article 101 with an appearance more similar to cloth underwear.

Furthermore, as shown in FIG. 8a and FIG. 9, the absorbent article 101 comprises a front elastic component 130 and a back elastic component 131 which are both based on a number of elastic threads mounted at a certain distance from each other in a generally parallel manner around the article 101, i.e. the region of the belly and the backside of the user. The purpose of these elastic components 130, 131 is to contribute to a good fit and comfort for the wearer of the article 101. In particular, the configuration of the elastic threads can be adapted to the male and female anatomy and the need for a suitable fit and comfort for male and female users of the article 101.

The positioning of the elastic threads and also the elastic properties of the elastic threads can be individually adapted so as to provide a configuration of the back elastic component 131 and front elastic component 130 which is arranged so as to individually fit the male and female anatomy, respectively. This will be described in greater detail below with reference to FIG. 13a and FIG. 13b. More precisely, the positioning of the elastic threads refers to the manner in which the threads are laid out, in a geometric sense, along the absorbent articles in the array and also the distance between any two adjacent elastic threads. According to a further embodiment, the number of elastic threads used can also be chosen so as to provide a configuration of the back elastic component 131 and front elastic component 130 which is arranged so as to individually fit the male and female anatomy, respectively.

Furthermore, and as mentioned above, it can be noted that a process of fastening the elastic waist component 123 and the elastic leg component 124 close to an edge of a web material, i.e. in this case close to the waist edges 107, 108 and the leg edges 109, 110, respectively, is difficult due to the manufacturing tolerances of the production line. The provision of elastic elements along the edges of the article, i.e. along the waist, legs and crotch edges, contributes to a modern and well-fitting absorbent article such as an incontinence article. Such elastic elements are normally provided with a number of elastic threads which are arranged along a waist edge, a leg edge and two crotch edges.

A production process for a pant-type absorbent article operates at a high rate and such a fully automatized manufacturing line needs to have a certain tolerances. If the elastic threads of the elastic components are positioned too close to the corresponding edges, there is a risk that the threads may actually be laid and positioned outside the edges. Since glue is normally applied to the threads, there is a risk for production interruption if the elastic threads are erroneously positioned outside the actual edges of the article.

With further reference to FIG. 9 and also FIG. 8b, there is provided an embodiment in which the elastic waist component 123, the elastic leg component 124 and the elastic absorbent body components 125, 126 are fastened by means of a folding arrangement of the article 101 in question. The principles for this folding arrangement are shown in FIG. 8b, which shows an enlargement of a small section of the upper part of the back portion 104, more precisely a section of the absorbent article 101 close to the waist edge 108 of the back portion 104.

In a manner which is conventional as such, the absorbent article 101 comprises a liquid permeable topsheet 132, i.e. a sheet which is intended to face the user of the article 101, and a liquid impermeable backsheet 133, i.e. a sheet which is placed so as to face the garment worn by the user. Generally, the liquid permeable topsheet 132 comprises or consist of a nonwoven material. The topsheet material may further be composed of tow fibres, porous foams, apertured plastic films and similar materials. The materials suited as topsheet materials should be soft and non-irritating to the skin and should be readily penetrated by body fluid, e.g. urine or menstrual fluid, and display low rewetting properties.

Preferably, coloured non-woven material is used for the topsheet 132, preferably having the same or substantially the same colour as at least the fabric layers of the article which define the colour of the outside of the article. The absorption zone, i.e. where the core is located, is preferably of a lighter colour as a result of the core, which may be entirely in relatively light colours, shining through the non-woven material of the topsheet 132.

Preferably, coloured material is also used for the backsheet 133, preferably the same colour as the topsheet 133.

Furthermore, the liquid impermeable backsheet 133 may consist of a thin plastic film, e. g. a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapour to escape from the absorbent article, while still preventing liquids from passing through the backsheet 133 material.

According to various embodiments, the materials which can be used for manufacturing the backsheet 133 include thin and flexible fluid impermeable plastic films, or fluid impermeable nonwoven materials, fluid impermeable foams and fluid impermeable laminates.

Furthermore, the backsheet 133 is formed by a single layer, and can alternatively be formed by a multi-layered structure, i.e. a laminate, wherein at least one layer is fluid impermeable. Furthermore, the backsheet 133 can optionally be elastic in either direction. According to further embodiments, the backsheet 133 may be breathable, implying that air and vapor may pass through the backsheet. Furthermore, the backsheet 133 may optionally have an outer, garment-facing surface of a textile material such as nonwoven.

The absorbent core 117 can be formed by a single layer consisting of fibres of cellulosic fluff pulp. According to alternative embodiments, the absorbent core 117 can be made up of any suitable absorbent or fluid-absorbing material as known in the art, for example foam, fiber waddings and similar materials.

Furthermore, the absorbent core 117 may consist of a mixture of cellulosic fluff pulp and a suitable amount of superabsorbent particles. Such superabsorbent material is well known in the field of absorbent articles, and is constituted by a water-swellable and water-insoluble material which is capable of absorbing large quantities of fluid upon formation of a hydrogel. Normal superabsorbent materials are capable of absorbing fluids of at least 10 times its own weight.

According to further embodiments, the absorbent core 117 may further incorporate components for improving the properties of the absorbent core. Some examples of such components are binder fibers, fluid-dispersing materials, fluid acquisition materials, etc. as known in the art. The absorbent core 117 may also be a homogeneous structure or may be a layered structure with laminates of the same or different materials. The absorbent layers may have uniform thickness or may vary in thickness in different parts of the layers.

The layers or fabrics forming at least the top side of the core are preferably of lighter colours, preferably at least lighter than the topsheet 132, for example L* values above 90, for example white or substantially white.

The topsheet 132 and backsheet 133 may be connected to each other for example by adhesive bonding, gluing or welding by heat or ultrasonic. The topsheet 132 and/or the backsheet 133 may further be attached to the absorbent body by any method known in the art, such as adhesive, heat-bonding etc.

According to an embodiment, the topsheet and backsheet, herein also called inner and outer fabrics, in the portions forming the front portion 103 and the back portion 104 may be of different type than the topsheet and backsheet in the crotch portion 105. In the latter case, it is suitable with a fluid-permeable topsheet and a fluid-impermeable backsheet (as described above) since the absorbent article 101 must have absorbent properties in the crotch portion 105. However, in the parts forming the front portion 103 and the back portion 104, both the topsheet and the backsheet may be for example liquid-impermeable, since these parts of the absorbent article 101 generally do not need to have absorbent properties. The fabrics or materials used for this topsheet and backsheet in the front and back portions 103, 104 are preferably coloured, preferably in the same colour as the topsheet 132 in the crotch portion.

According to the embodiment shown in FIG. 8b, the backsheet 133 is configured so that it can be folded along the waist edge 108 of the back portion 104 and over the topsheet 132. In this manner, the elastic waist component 123 is at least partly enclosed between the topsheet 132 and the backsheet 133. More precisely, the elastic waist component 123 is positioned between the backsheet 133 and the topsheet 132, and the backsheet 133 is then folded over the topsheet 132. In this manner, an edge 134 of the backsheet 133 is defined along the inside of the absorbent article 101, i.e. facing the user of the article.

The embodiment shown in FIG. 8b is configured so that the elastic waist component 123 is fully enclosed by means of the topsheet 132 and the folded backsheet 133. However, according to other embodiments (as will be described below with reference to FIG. 11e), the backsheet 133 and the elastic waist component 123 may be dimensioned and configured so that the backsheet 133 is folded in a manner so as to enclose only a part of the elastic waist component 123.

A similar folding process is carried out also as regards the front portion 103, so that the backsheet 133 forms a fold defining an edge 135 (see FIG. 8a) along the inside of the absorbent article 101. Furthermore, a similar folding process is carried out also as regards the crotch portion 105, so that a fold is formed with a first edge 136 and a second edge 137 (see FIG. 8a) along the absorbent body 117 in the crotch portion 105. Also, a similar folding process is carried out also so as to enclose the elastic leg component 124 along the leg edges 109, 110.

The purpose of the folding procedure as described above is to allow the elastic elements, i.e. the elastic waist component 123, the elastic leg component 124 and the elastic absorbent body components 125, 126, to be positioned very close to the corresponding edge of the absorbent article 101. This means that the absorbent article 101 can be manufactured in a manner with so that it resembles an ordinary undergarment which has an optimized waist elastic function and which is convenient to wear. By positioning the elastic elements very close to each edge of the article, the amount of unelasticized web material which otherwise may occur along the edges can be avoided. In summary, the absorbent article 101 will be more similar in look and feel to regular underwear, while still offering sufficient protection against urine leakage. Furthermore, in an array of gender-specific absorbent articles, an elastic waist component, an elastic leg component and an elastic absorbent body component can be adapted in a suitable manner in article intended to be worn by a male and female user, respectively.

Consequently, the backsheet 133 or the topsheet 134 is folded along the waist edges 107, 108, leg edges 109, 110 and crotch edges 128, 129 so as to enclose each corresponding elastic element 123, 124, 125, 126. Certain alternative embodiments will be further described below.

Figure 10:
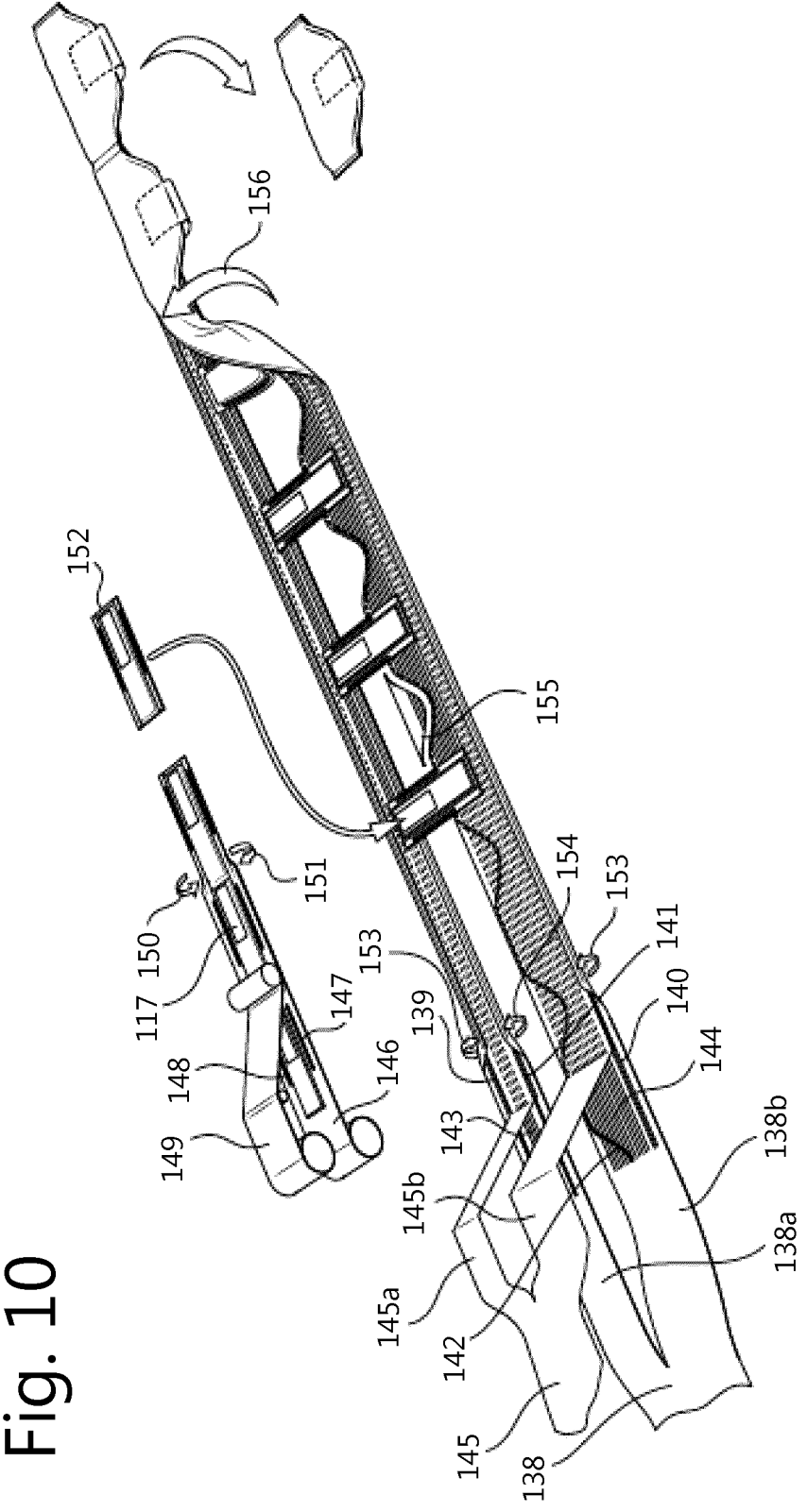

The positions and the elastic properties of at least the elastic threads forming the front elastic component 130 and the back elastic component 131 can be varied in order to provide articles which are adapted to the male and female anatomy and to other requirements regarding male and female absorbent products. An example embodiment of a manufacturing line for a pant-type absorbent article 101 is schematically illustrated in FIG. 10.

A first continuous sheet 138 of web material is supplied and is also divided, in a lengthwise manner, so as to form a first web section 138a and a second web section 138b. The first web section 138a forms the basis of a backsheet for the front portion 103 (see FIGS. 8 and 9) of the absorbent article 101, whereas the second web section 138b forms the basis of a backsheet for the back portion 104.

A plurality of strips of elastic material are attached to the first and second web sections 138a, 138b in a tensioned state. More precisely, a first strip 139 and a second strip 140 of elastic material form the basis of the elastic waist component 123, and a third strip 141 and a fourth strip 142 of elastic material form the basis of the elastic leg component 124. Also, a fifth strip 143 and a sixth strip 144 of elastic material form the basis of the front elastic component 130 and the back elastic component 131, respectively.

The strips 139, 140, 141, 142, 143, 144 of elastic material may be glued or otherwise fastened to the continuous sheets 138a, 138b of web material, and said strips are intended to form an elastic web feature of the absorbent article 101 as described above with reference to FIGS. 8-9.

Next, a further continuous sheet 145 of web material is provided and is split longitudinally in order to form a third web section 145a and a fourth web section 145b. The third web sections 145a forms the basis of a topsheet for the front portion 103 whereas the fourth web section 145b forms the basis of a topsheet for the back section 104.

The third web section 145a and the fourth web section 145b are joined to the first web section 138a and the second web section 138b, respectively, in order to form a laminated product having the strips 139, 140, 141, 142, 143, 144 of elastic material sandwiched between the first web section 138a and the third web section 145a, and also between the second web section 138b and the fourth web section 145b. The second sheets may be attached to each other by ultrasonic bonding, welding, adhesive, embossing, mechanical fastening, or the like. The attachment of the above-mentioned web sections and elastic strips is here described as being performed in consecutive steps but these steps are typically performed in a single step.

In order to form the crotch portion 105 (see FIG. 8a) with its absorbent core 117, a third continuous sheet 146 of web material is provided and forms the basis of a backsheet for the crotch portion 105. The absorbent core 117 is then laid out on the third continuous sheet 146. Also, a seventh strip 147 and an eighth strip 148 of elastic material are also laid out on the third sheet 146 of web material. The seventh strip 147 of elastic material forms the basis of the first absorbent body elastic 125 (see FIGS. 8a and 9), whereas the eighth strip 148 of elastic material forms the basis of the second absorbent body elastic 126.

Next, a fourth continuous sheet 149 of web material is provided and is joined to the third continuous sheet 146, suitably in a manner which is similar to that described above with reference to the first web section 138a, the second web section 138b, the third web section 415a and the fourth web section 145b. During this process, the seventh strip 147 and eighth strip 148 of elastic material, as well as the absorbent core 117, are sandwiched between said third continuous sheet 146 of web material and said fourth continuous sheet 149 of web material.

In order to adapt the manufacturing process to a male-type article and a female-type article, respectively, the process can be modified by choosing suitable elastic material (i.e. for the strips 139, 140, 141, 142, 143, 144 of elastic material) to be included in the articles. Such selections of elastic material according to dimensions, brand, elastic properties and other parameters must be implemented in the manufacturing process in an efficient manner generally without any interruptions or time-consuming modifications.

A folding procedure is next carried out so as to fold the edges of the crotch portion 105 and form the edges 136, 137 on the crotch portion 105. This folding operation is indicated in a simplified manner with the arrows 150 and 151 in FIG. 10. Similarly, folding of the front portion 103 and the back portion 104 is indicated in FIG. 10 with arrows 153, 154 in a simplified manner. This folding operation corresponds to that which is shown in FIG. 8b.

In a further manufacturing step, the web formed by means of the third sheet 146 of web material, the fourth sheet 149 of web material 149 and the absorbent core 117, is cut into individual pieces 152, each of which forms the above-mentioned crotch portion 105 which is subsequently attached to the web formed by the first and second web sections 138a, 138b and the third and fourth web sections 145a, 145b. In this regard, the crotch portions 105 are laid out at a predetermined distance so as to bridge the front portion 103 and the back portion 104 and to form the basis of the finished absorbent article. As shown in FIG. 10, a piece 152 which forms a crotch portion 105 is laid out in a transversal direction in relation to the webs forming the front portion and the back portion.

The crotch portion 105 may be attached to the chassis using any known fastening technology, such as ultrasonic bonding, welding, adhesive, embossing, mechanical fastening, or the like. In this manner, a complete chassis is formed for the article 101 in question.

In a subsequent manufacturing step, leg openings 155 are cut out of the laminated web material forming the chassis of finished absorbent articles. The cutting may be performed by any type of suitable cutting equipment (not shown in FIG. 10), such as rolling cutting using two opposite rollers.

Next, the first and fourth web sections 138*b*, 145*b* are folded to form the final product, such that the first web section 138*b* becomes a backsheet of the chassis and the fourth web section 145*b* becomes the topsheet of the chassis. This folding is shown with an arrow 156 in FIG. 10. After for example welding of side seams, the continuous assembly of products is cut into individual absorbent articles by means of cutting equipment (not shown in FIG. 10).

Figures 11A, 11B, 11C:
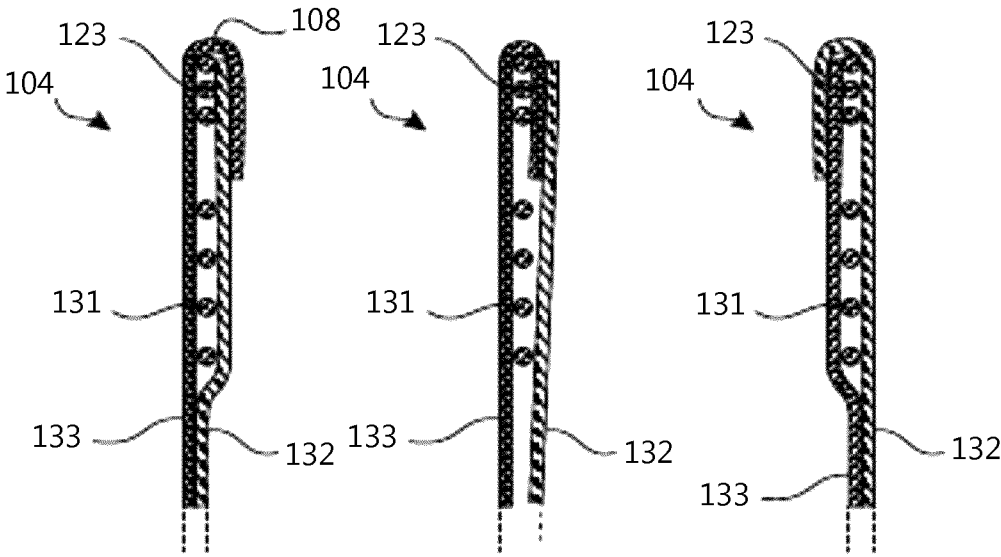
FIGS. 11A-11F show cross-sectional views of alternative embodiments of the absorbent article according to the disclosure.

FIGS. 11*a-f* show cross-sectional views of alternative embodiments of the structure forming the back portion 104. FIG. 11*a* shows an embodiment in which the elastic element 123 is sandwiched between an inner side of the backsheet 133 and an inner side of the topsheet 132. The above-mentioned back elastic component 131 is also shown in FIG. 11*a*. Also, the backsheet 133 is folded over an outer side of said topsheet 132 so as to enclose the elastic element 123 and so as to define the edge 134. This procedure corresponds to the embodiment shown in FIG. 8*b* and FIG. 3.

Furthermore, FIG. 11*b* shows an alternative embodiment in which the elastic element 123 is enclosed and covered within a fold which is defined by the backsheet 133. Subsequently, the topsheet 132 is attached to said backsheet 133, suitably by gluing.

FIG. 11*c* shows a further alternative embodiment in which the elastic element 123 is sandwiched between an inner side of the backsheet 133 and an inner side of the topsheet 132, and wherein the topsheet 132 is then folded over an outer side of said backsheet 133 so as to enclose the elastic element 123.

Figures 11D, 11E, 11F:
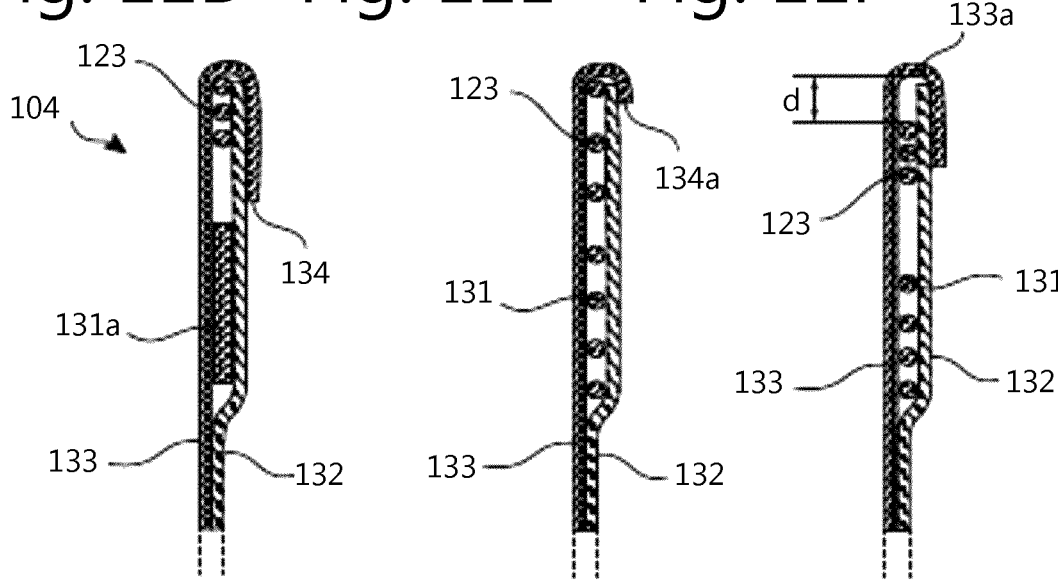

FIG. 11*d* shows a further alternative embodiment which generally corresponds to the embodiment shown in FIG. 11*a*, but having a back elastic component 131*a* which is in the form of a relatively thin strip manufactured from an elastically stretchable film. As an example, a suitable thermoplastic elastomer can be used for such a stretchable film.

Furthermore, FIG. 11*e* shows a further alternative embodiment which generally corresponds to the embodiment shown in FIG. 11*a* but which shows a configuration in which the backsheet 133 is folded in a manner so that it partly encloses the elastic element 123. Consequently, this embodiment is arranged with a backsheet 133 and an elastic element 123 having other dimensions and configurations than the embodiment shown in FIG. 11*a*, so that the edge 134 is closer to the waist edge 108 (see also FIG. 8*b*) as compared with the embodiment in FIG. 11*a*. Even though the elastic element 123 is only enclosed partly by the folded portion of the backsheet 133, the article can be designed in a manner which is similar to regular underwear while still providing relevant protection against incontinence and also sufficient comfort and fit.

Variations of the embodiments shown in FIGS. 11*d* and 11*e* but where the topsheet and backsheet are folded as in FIG. 11*b* and FIG. 11*c*, respectively, are also possible.

FIG. 11*f* shows an embodiment in which the elastic element 123 is positioned at a certain distanced from the inside of the fold 133*a* which is defined by the backsheet 133. According to embodiments, the distance d from the inside of the fold 133*a* is less than 10 mm, preferably less than 5 mm, and most preferably less than 3 mm, in order to provide an absorbent article 101 which is similar to regular underwear while still offering sufficient protection against urine leakage.

Figure 12:
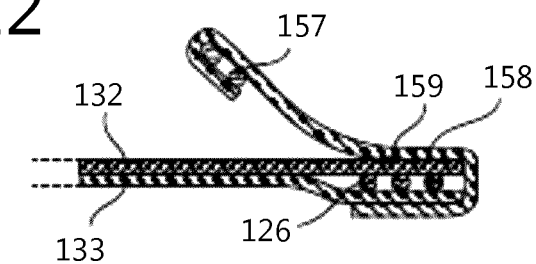

Furthermore, FIG. 12 shows a cross-sectional view of an embodiment involving the crotch section 105 and in particular showing the second absorbent body elastic 126 (see also FIG. 8*a* and FIG. 9). According to this embodiment, the crotch portion comprising a further web material 158 which is folded over the laminate which is defined by the topsheet 132 and the backsheet 133. In this manner, the second absorbent body elastic 126 is enclosed. According to a further embodiment, the crotch portion 105 can be equipped with so-called standing gathers comprising elastic elements 157 which are enclosed by a section of the further web material 158 which is attached to the topsheet 132 by means of adhesive 159 or another suitable fastening means. A similar arrangement can be made as regards the first absorbent body elastic 125 (see FIG. 8*a* and FIG. 9).

Figure 13A:
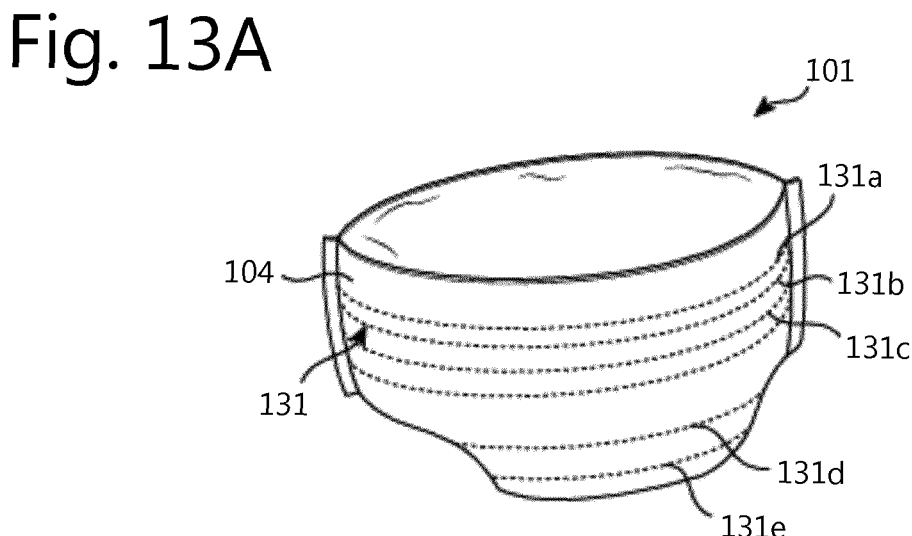
FIG. 13A is a perspective view of the absorbent article as seen from the rear, showing a first configuration which is adapted for the male anatomy.
Figure 13B:
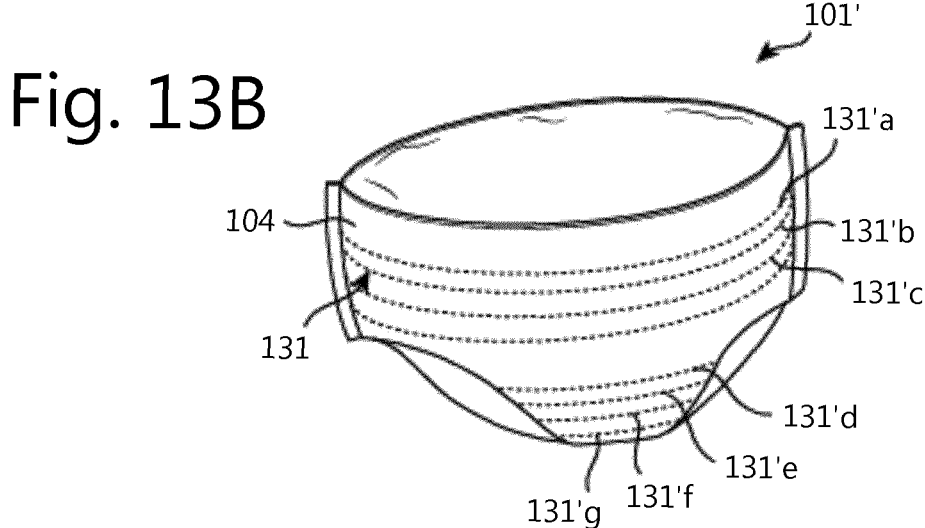
FIG. 13B is a perspective view of the absorbent article as seen from the rear, showing a second configuration which is adapted for the female anatomy.

FIG. 13*a* and FIG. 13*b* are perspective views, as regarded from the rear of an absorbent article 101, 101', wherein FIG. 13*a* shows a first configuration of an embodiment of the absorbent article 101 and FIG. 13*b* shows a second configuration of an embodiment of the absorbent article 101'. The first configuration describes a male type of absorbent article 101, whereas the second configuration describes a female type of absorbent article 101'.

As indicated in FIG. 13*a*, the article 101 is provided with a back elastic component 131 which according to an embodiment comprises an upper section with a plurality of elastic threads 131*a*, 131*b*, 131*c* etc., which are mounted along the article 101 at a predetermined distance from each other, and also a lower section with a further plurality of elastic threads 131*d*, 131*e*, which are also mounted at a predetermined distance from each other. The elastic threads are mounted during the manufacturing process, as described above with reference to FIG. 11, in a generally parallel manner in the back portion 104, i.e. around the region of the article 101 which corresponds at least to the backside of the user. The distance between the elastic threads 131*a-e* and the extension of said threads 131*a-e* are chosen so as to suit a male user, i.e. adapted for the male anatomy and requirements regarding style, cut, comfort and fit for a male user. Also, the elastic properties of the elastic threads 131*a-e*, in particular as regards the dimensions, elastic force and choice of material, are selected in a corresponding manner to suit a male user of the article 101.

Referring now to FIG. 13*b*, which is an article 101" suitable for a female user, it can be seen that this article 101" has a design which is similar to the article 101 shown in FIG. 13*a*, i.e. including a back elastic component 131" comprising an upper section with a plurality of elastic threads 131"*a*, 131"*b*, 131"*c* etc. which are positioned in the same manner as the upper section shown in FIG. 13*a*. However, the back elastic component 131" comprises a lower section which is different from the lower section shown in FIG. 13*a*. More precisely, the lower section of the back elastic component 131" in FIG. 13*b* has a higher number of elastic threads 131"*d*, 131"*e*, 131"*f*, 131"*g* than the lower section shown in FIG. 13*a*. Also, the threads 131"*d*, 131"*e*, 131"*f*, 131"*g* in FIG. 13*b* may be of different type than the threads shown in FIG. 6*a* in order to adapt the article 101" according to FIG. 13*b* for the female anatomy and also requirements regarding style, cut, comfort and fit suitable for a female user.

Also, although not visible in FIG. 13*b*, the elastic threads 131"*d*, 131"*e*, 131"*f*, 131"*g* of the lower section in FIG. 13*b* may also have elastic properties—i.e. as regards the dimensions, elastic force and choice of material—which are suitable for a female user and which properties consequently are different than those of the corresponding elastic threads 131*d*, 131*e* shown in FIG. 13*a*.

The male and female absorbent articles 101, 101″ may differ as regards various features, for example:

the number of elastic threads used in the back elastic components 131, 131″;

the elastic properties of the elastic threads 131, 131″;

the positioning of the threads and the distance between adjacent threads.

For example, the absorbent article 101 in FIG. 13*a* may have a lower section with two elastic threads, whereas the corresponding lower section in the absorbent article 101″ shown in FIG. 13*b* may have four elastic threads.

Combinations of different features can be made in order to meet the requirements for male and female absorbent products.

Furthermore, according to an embodiment, a male article 101 (see FIG. 6*a*) may comprise a number of elastic threads of approximately 540 dtex, whereas a female article 1″ (see FIG. 13*b*) may comprises a number of elastic threads of approximately 800 dtex, where dtex represents a unit of the linear density of a continuous filament or yarn of the corresponding elastic thread. This means that the lower section of the female article 101″ is configured so as to provide a higher elastic force—as indicated by means of arrows in FIG. 13*b*—to pull the lower section of the article 101″ together to fit a female wearer.

Furthermore, although not shown in FIGS. 13*a* and 13*b*, it should be noted that the upper sections of the male and female articles 101, 101″ also may have different elastic properties, i.e. in a similar manner as the lower sections.

FIG. 13*a* and FIG. 13*b* indicate that the articles 101, 101′ for male and female users, respectively, are slightly different in cut and design. It should be noted that the above-mentioned adaptations for male and female users, respectively, are made without departing from the goal of an efficient manufacturing process as discussed above.

According to an embodiment, a manufacturing process in which a change between production of a male and a female product must be carried out can be made by simply switching the elastic threads adapted for a male article for other elastic threads (having other dimensions or elastic properties) adapted for a female article. Alternatively, the distance between the threads can be changed during such an operation. This also means that the leg opening of the articles can be cut in a similar manner, and with the same equipment, for both male and female articles.

Referring to FIGS. 14*a* and 14*b*, respectively schematically showing the inside and outside of articles according to FIGS. 1-13, embodiments using coloured materials for the inner and outer fabrics will now be described.

The following of the above mentioned fabrics are examples of inner fabrics of an elastic film laminate pant according to FIGS. 1-7 and according to the present disclosure: inner layer(s) 21 or 36 of laminate 20, the inside of waist band 18, backsheet 25 (can also be an outer fabric), topsheet 26, cover strip 35. These are the materials or fabrics of which at least a part in use faces the user's skin. The inner fabrics are part of a plurality of fabrics which define the colours of the inside surface of the absorbent article.

The following of the above-mentioned fabrics are examples of outer fabrics of an elastic film laminate pant according to FIGS. 1-7 and according to the present disclosure: outer layer(s) 22 or 38 of laminate 20, the outside of waist band 18, crotch panel material 24 and/or backsheet 25. These are the materials or fabrics of which at least a part in use faces the user's clothing. The outer fabrics are part of a plurality of fabrics which define the colour of the outside surfaces of the absorbent article.

The following of the above mentioned fabrics are examples of inner fabrics of threaded pant according to FIGS. 8-13 and according to the present disclosure: topsheet 132 for the back and front section 4 and topsheet 132 for crotch section. These are the materials or fabrics of which at least a part in use faces the user's skin. The inner fabrics are part of a plurality of fabrics which define the colours of the inside surface of the absorbent article.

The following of the above mentioned fabrics are examples of outer fabrics of a threaded pant according to FIGS. 8-13 and according to the present disclosure: back-sheet 133 for front and back section 3, 4 and backsheet for crotch portion. These are the materials of which at least a part in use faces the user's clothing. The outer fabrics are part of a plurality of fabrics which define the colour of the outside surfaces of the absorbent article.

The colour of the inside and outside surfaces, or portions thereof, may result from the combination of all layers of the fabric, depending on e.g. the density and colour of a non-woven fabric and the resulting transparency or opacity.

FIG. 14*a* shows the inside surface of the absorbent article with the inside surface portions 45*a*, 46*a* of respectively the front and back portions 5, 6 of the chassis or waist portion. The connecting or crotch portion 19 comprises, on top, the liquid-permeable topsheet 26, which has an outer zone 43 surrounding the absorbent core 2, also referred to as a surrounding zone on the topsheet, adjacent to and at least partly surrounding an inner absorption zone 42 above the core 2. In embodiments, within the absorption zone 42, a central region 41 may be distinguishable by presence of an acquisition layer on top of the core 2. These are the portions of the inside surface which in use faces the user's skin. The inside surface portions comprise a plurality of fabrics/materials which define the colours of the inside surface of the absorbent article. The inside surface portions 45*a*, 46*a* of respectively the front and back portions 5, 6 and the topsheet with its different zones are examples of different portions of the inside surface.

FIG. 14*b* shows the outside surfaces with outside surface portions 45*b*, 46*b* of respectively the front and back portions 5, 6 of the chassis or waist portion. The connecting or crotch portion 19 comprises on the outside a zone 44 which may be formed by the crotch panel material 24, such as a backsheet, described above. These are the materials which in use faces the user's clothing. The outer fabrics are part of a plurality of fabrics which define the colour of the outside surfaces of the absorbent article. The outside surface portions 45*a*, 46*a* and zone 44 are examples of different portions of the outside surface.

In embodiments at least the outer portions 44, 45*b*, 46*b* and the zone 43 on the liquid-permeable topsheet (at least partly) surrounding the absorption zone 42 have, in the CIE L*a*b* colour space, measured as described below, L* values less than 80 and mutual colour differences ΔE*ab less than 10, i.e. these fabrics are coloured with substantially the same colour. Preferably, also the inside surface 45*a*, 45*b* have substantially this same colour.

The absorption zone 42 has an L* value less than 90 and a colour difference ΔE*ab more than 5 with respect to zone 43 surrounding the absorption zone and/or the outer portion 45*b*, 46*b*. The absorption zone is thus also coloured for reasons of discreetness while having a noticeable colour difference with the surrounding zone and/or outside fabrics, so that the user can distinguish the inside of the article from the outside and/or is reassured that the absorbent core is present.

In embodiments, according to the second aspect of the present disclosure, the outside portions 44, 45b, 46b have, in the CIE L*a*b* colour space, L* values less than 80 and mutual colour differences ΔE*ab less than a predetermined limit, for example 10, and the inner portion 26 (topsheet per se), 45a, 46a have L* values less than 90 and mutual colour differences ΔE*ab more than said predetermined limit. This means that the inside as well as the outer fabrics are coloured, with more colour difference on the inside than on the outside.

In embodiments according to the disclosure, the absorption zone 42 may have a colour difference ΔE*ab more than 10 with respect to said zone 43 surrounding the absorption zone and/or said outside fabrics 44, 45b, 46b. A higher ΔE*ab is preferred in view of more clearly indicating the absorption zone 42 to the user.

In embodiments according to the disclosure, the absorption zone 42 may have a colour difference ΔE*ab less than 40 with respect to said zone 43 surrounding the absorption zone and/or said outer surface. It is preferred that this ΔE*ab is not too high in view of discreetness of the article.

In embodiments according to the disclosure, the indication of the absorption zone 42 may be provided by the absorbent core 2, or at least an upper layer thereof, being visible through the topsheet 26. With other words a difference in colour in reference to the rest of the product is created. This means that the colour difference of the absorption zone 42, which indicates its presence to the user, may be achieved by the visibility of the core 2 or upper layer thereof, through the topsheet 26. In this way, the presence of the absorbent core can be indicated to the user without the need of providing print or other indications on the topsheet 26 itself.

The visibility of the absorbent core 2, or at least an upper layer thereof, may for example be achieved by the core 2 being made of a fabric which has a higher L* value (i.e. has a lighter colour) than the topsheet 26. The colour of the absorption zone 42 thus results from the combination of the colours of the absorbent core 2 and the topsheet 26 (which is preferably per se entirely of the same colour/fabric) and may have a higher L* value (i.e. have a lighter colour) than said zone 43 surrounding the absorption zone, ΔL* between these zones being more than 5, preferably more than 10 and less than 35.

In embodiments, the fabric of the absorbent core 2 or upper layer thereof may have an L* value of more than 80, i.e. be of a light colour which may be clearly visible through the topsheet 26. The absorbent core 2 refers to the absorbent core 2 in FIGS. 1-7. The absorbent core may also refer to the absorbent core 117 in FIGS. 8-13. The same applies to the topsheet 26 which refers to the topsheet 26 in FIGS. 1-7. That is, the topsheet 26 may also refer to the topsheet 132 in FIGS. 8-13.

In embodiments according to the disclosure, all the inside and outside surface portions 26, 44, 45a-b, 46a-b, except in the absorption zone 42, may have L* values less than 80, preferably less than 60 (i.e. have relatively dark colours), and/or mutual colour differences ΔE*ab less than 10. It has been found that darker colours are preferred by users for reasons of discreetness and/or more underwear-like appearance.

In embodiments, the articles may be fully coloured i.e. they have a base colour which consist of a primary colour such as black, red, blue, violet, orange, yellow, green and indigo, as well as any other hue or mix thereof. These colours may also be mixed with white . . . That is, the sheets of material, i.e. the plurality of fabrics which define the colour of the outside and inside of the pant article may be white or fully coloured, i.e they have a base colour which consist of a primary colour such as black, red, blue, violet, orange, yellow, green and indigo, as well as any other hue or mix thereof. These colours may also be mixed with white. The colour can be added to the material either upon manufacture of it, for example by impregnating, or supplied afterwards by known print techniques. Examples of print technique can be flexography, ink-jet printers etc. The colouration may be made by impregnation of a colourant into a substrate. Colourants such as dyes, pigments, or combinations may be impregnated in the formation of substrates such as polymerics, resins, or nonwovens. For example, the colourant may be added to molten batch of polymer during film, fiber, or filament formation. All methods are well known in the art. As an example, in order to get a fully coloured product if the outer and/or inner fabric/fabrics which faces the user's clothing or the user's skin are white the fabric layer underneath should be coloured.

In embodiments, the fully coloured pant articles may have a graphic pattern to resemble conventional textile underwear even more. The fully coloured pants may be designed with a print applied onto the fully coloured product, for example on the outside, such as flowers or butterflies.

As described in connection to FIGS. 1-13 the backsheet may have a plastic sheet. This sheet may also be coloured. The plastic sheet may also be fully coloured A coloured plastic sheet may influence the colour of the absorbent article. The same applies to the elastic film in the waist portion for an elastic film laminated absorbent product. The plastic film or the elastic film may also be white if the nonwoven is/are fully coloured.

Colour Measurement

Colour is determined within the L*a*b* colour space, as established by the Commission Internationale de l'Éclairage (CIE) in 1976. The colour space is divided into three axes. L* represents lightness and the axis extends from 0 (black) to 100 (white). The axis a* goes from green to red, where positive values indicate more saturated red, and negative values more saturated green. The b*-axis goes from blue to yellow, where positive values represent more saturated yellow and negative values more saturated blue. This colour space is well known in industry and is generally referred to as CIE L*a*b* or CIELAB (1976).

A suitable spectrophotometer is available from Konica-Minolta, under the designation CM-5 (equivalent apparatuses can also be used). The apparatus illuminates the sample diffusely and detects the light at 8 degrees to the normal line (a geometry named di:8°, de:8°). The instrument is set to SCE (specular component excluded). Standard Illuminant D65 is utilized, and the viewing angle is set to 10°. Normally the diameter of the measured area should be 30 mm. However if the relevant sample areas are smaller (having a diameter less than 30 mm) then smaller spectrophotometer apertures are utilized (as large as possible without transgressing the relevant colour area).

A difference between two colours in the colour space CIE L*a*b* is characterised by a Delta E-value (ΔE*ab). The differences between the colours on the three respective axes are squared in this, following which the differences are summed and the root derived from the sum:

$$\Delta E_{ab}^4 = \sqrt{(L_2^* - L_1^*)^2 + (a_2^* - a_1^*)^2 + (b_2^* - b_1^*)^2}$$

The following measurement procedure may be used. The pant part with the portion to be measured is placed over the recording aperture of the instrument. In particular, the sample is placed flat and smooth over the spectrophotometer aperture. Any elastic elements should remain in their contracted or non-stretched state. A white ceramic tile (available from Konica-Minolta) is placed on (above) the sample, as a standard backing. The ceramic tile has values L* 96.0, a* 0.1 and b* 2.85. The recording aperture of the instrument is placed against the sample/products. The measurement can then begin. Since the absorbent articles are in the form of pants, the sides, of which the front portion and back portion have been joined in a seam may be torn/clipped. However, the measurements may also be performed on a product where the reams not have been torn/clipped.

EXAMPLES

The above procedure was used for the examples mentioned below.

The absorbent articles are in the form of pants, the sides, of which the front section and back section are joined in a seam. The measurements were performed on products which the seams were not torn/clipped.

The portion of the absorbent article which was to be measured was placed over the (normally 30 mm diameter) aperture, and then a white ceramic tile on top. The portion is placed flat and smooth over the spectrophotometer aperture. Any elastic elements should remain in their contracted or non-stretched state. A white ceramic tile (available from Konica-Minolta) is placed on (above) the sample, as a standard backing. The ceramic tile has values L* 96.0, a* 0.1 and b* 2.85. The white tile mimics the user's pale skin when looking at the diaper from the outside The recording aperture of the instrument is placed against the sample/products. The measurement can then begin. In the examples below the tile will not shine through so much, but for a very thin chassis or a thin nonwoven laminate it can make the L-value higher Example 1

Black Threaded Pant Article Similar Construction as the Pant Described in Connection with FIGS. 8-13

The waist panel, is formed of a laminate consisting of two inelastic black nonwoven layers where elastic threads have been placed between. The elastic threads are laid crosswise in the transverse direction of the article. Examples of elastic threads are sold under the LYCRA trademark. The two nonwoven layers are connected to one another by two methods, construction adhesive coated on one of the nonwoven and elastic adhesive coated on the elastic threads between the nonwoven layers. The two nonwoven layers are formed from hydrophobic spunbond and have a weight per unit area of 18 gsm (Gram per Square Meter) respectively. In this example a black spunbond nonwoven 18 gsm from Avinti was used.

The backsheet under the core comprises the same nonwoven as for the waist panel and it is attached to a coloured plastic film of polyethylene with a weight per unit area of 15 gsm for black product (non breathable film) The film has the following value: L*=26.3, a*: –0.1 and b*=–0.3. The film was measured as a single ply, with a white ceramic tile as background (the tile has values L* 96.0, a* 0.1 and b* 2.85). The same tile is used as background in all of our measurements, but on materials as thin as a single ply backsheet film it influences a bit more than on more massive and opaque objects.

The topsheet over the core and an area outside the core is liquid-permeable and is of a spunbonded, 16 gsm hydrophilic material. For this threaded product a spunbond Non woven 16 gsm from Fitesa was used.

The product had a white absorbent core underneath the coloured topsheet. The following values was measured on the different portions.

| Example 1 | L* | a* | b* |
|---|---|---|---|
| Panel (outside, portions 45b, 46b) | 18.0 | 0.63 | 1.87 |
| Backsheet under core (zone 44) | 22.9 | 0.63 | 1.72 |
| Topsheet over core (zone 42) | 35.1 | 0.86 | 4.63 |
| Topsheet area outside of the core (surrounding zone 43) | 18.5 | 0.46 | 1.47 |

ΔE*ab between Panel and Backsheet under core: 4.95
ΔE*ab between Topsheet over core and Backsheet under core: 12.52
ΔE*ab between Topsheet over core and Topsheet area outside of the core; 16.19

Example 2

Black Elastic Film Laminate Pants—Similar Construction as the Pant Described in Connection with FIGS. 1-7

The waist panel is formed of a laminate consisting of two inelastic black nonwoven layers where a black elastic film (35 gsm from Tredegar) has been placed between them.

The two nonwoven layers are formed from hydrophobic spunbond and have a weight per unit area of 16 g/m$^2$ respectively. For this product the following material has been used:

S-Tex Noir Cal 12% from Berry, Fiberweb France SAS. The two nonwoven layers are connected to the film by ultrasonic welding.

The backsheet under the core comprises the same nonwoven as for the waist panel has. The Non-woven is attached to a black colored plastic film of polyethylene with a weight per unit area of 15 gsm. The film has the following value: L*=26.3, a*: –0.1 and b*=–0.3. The film was measured as a single ply, with a white ceramic tile as background (the tile has values L* 96.0, a* 0.1 and b* 2.85). The same tile is used as background in all of our measurements, but on materials as thin as a single ply backsheet film it influences a bit more than on more massive and opaque objects.

The topsheet is liquid-permeable and is formed in this case of the same non-woven as the waist panel, i.e. spunbonded, 15.8 gsm S-Tex Noir Cal 12% from Berry, Fiberweb France SAS. The topsheet has been treated to become hydrophilic.

The product had a white absorbent core underneath the coloured topsheet. The following values was measured on the different portions.

| Example 2 | L* | a* | b* |
|---|---|---|---|
| Panel (outside, zones 45b, 46b) | 13.6 | 0.42 | 0.88 |
| Backsheet under core (zone 44) | 19.5 | 0.33 | 0.82 |
| Topsheet over core (zone 42) | 41.5 | 0.37 | 3.86 |
| Topsheet area outside of the core (surrounding zone 43) | 19.0 | 0.26 | 0.9 |

ΔE*ab between Panel and Backsheet under core: 5.88
ΔE*ab between Topsheet over core and Backsheet under core: 12.52
ΔE*ab between Topsheet over core and Topsheet area outside of the core: 22.69

Example 3

Burgundy Elastic Film Laminate Pants—Similar Construction as the Pant Described in Connection with FIGS. 1-7

The waist panel, is formed of a laminate consisting of two inelastic burgundy colored nonwoven layers where a black elastic film (35 gsm from Tredegar) has been placed between them.

The two nonwoven layers are formed from hydrophobic spunbond and have a weight per unit area of 16 g/m<2> respectively. For this product the following material has been used:

S-Tex Noir Cal 12% from Berry, Fiberweb France SAS. The two nonwoven layers are connected to the film by ultrasonic welding.

The backsheet under the absorbent core comprises the same non-woven material as for the waist panel. The Nonwoven is attached to a black coloured plastic film of polyethylene with a weight per unit area of 15 gsm The film has the following value: L*=42.2, a*=−25.5 and b*=−4.7. The film was measured as a single ply, with a white ceramic tile as background (the tile has values L* 96.0, a* 0.1 and b* 2.85). The same tile is used as background in all of our measurements, but on materials as thin as a single ply backsheet film it influences a bit more than on more massive and opaque objects.

The topsheet is liquid-permeable and is formed in this case of the same NW as the waist panel, i.e. spunbonded, 15.8 gsm S-Tex Noir Cal 12% from Berry, Fiberweb France SAS. The topsheet has been treated to become hydrophilic.

The product had a white core underneath the coloured topsheet. The following values was measured on the different portions.

| Example 3 | L* | a* | b* |
|---|---|---|---|
| Panel (outside, zones 45b, 46b) | 21.7 | 14.1 | −3.29 |
| Backsheet under core (zone 44) | 28.1 | 16.24 | −3.61 |
| Topsheet over core (zone 42) | 40.0 | 20.37 | −3.14 |
| Topsheet area outside of the core (surrounding zone 43) | 25.6 | 15.14 | −4.01 |

ΔE*ab between Panel and Backsheet under core: 6.69
ΔE*ab between Topsheet over core and Backsheet under core: 12.64
ΔE*ab between Topsheet over core and Topsheet area outside of the core: 15.37

Example 4

Pink-Beige Threaded Pants—Similar Construction as the Pant Described in Connection with FIGS. 8-13

The waist panel, is formed of a laminate consisting of two inelastic pink-beige coloured nonwoven layers where elastic threads have been placed between them. The elastic threads are laid crosswise in the transverse direction of the article. Examples of elastic threads are sold under the LYCRA or SPANDEX trademark. The two nonwoven layers are connected to one another by two methods, construction adhesive coated on one of the non-woven layers and elastic adhesive coated on the elastic threads between the nonwoven layers. The two nonwoven layers are formed from hydrophobic spunbond and have a weight per unit area of 18 gsm respectively. In this example a spunbond nonwoven 18 gsm from Avinti was used.

The backsheet under the core comprises the same NW as for the waist panel and it is attached to a colored plastic film of polyethylene with a weight per unit area of 20 gsm (pink, breathable film). The film has the following value: L*=83.5, a*=8.9 and b*=−8.6. The film was measured as a single ply, with a white ceramic tile as background (the tile has values L* 96.0, a* 0.1 and b* 2.85). The same tile is used as background in all of our measurements, but on materials as thin as a single ply backsheet film it influences a bit more than on more massive and opaque objects.

The topsheet over the core and an area outside the core is liquid-permeable and is of a spunbonded, 16 gsm hydrophilic material. For this threaded product a spunbond nonwoven 16 gsm from Fitesa was used.

The product had a white absorbent core underneath the coloured topsheet. The following values was measured on the different portions.

| Example 4 | L* | a* | b* |
|---|---|---|---|
| Panel (outside, portions 45b, 46b) | 70.2 | 11.9 | 13.26 |
| Backsheet under core (zone 44) | 78.9 | 10.15 | 12.07 |
| Topsheet over core (zone 42) | 86.8 | 5.45 | 12.47 |
| Topsheet area outside of the core (surrounding zone 43) | 73.1 | 9.14 | 10.21 |

ΔE*ab between Panel and Backsheet under core: 8.95
ΔE*ab between Topsheet over core and Backsheet under core: 9.19
ΔE*ab between Topsheet over core and Topsheet area outside of the core: 14.41

These examples show different kind of products having different kind of colours where the absorption zone are coloured for reasons of discreetness. The absorption zone, i.e. the topsheet over core has a noticeable colour difference with the surrounding zone and the outside surface, so that the user can distinguish the inside of the article from the outside and/or is reassured that the absorbent core is present. The portion: "Panel (outside, portions 45b, 46b)" in the tables above can also be considered being the inside portions of the panels since the same non-woven is placed on each side of the elastic film or threads, hence the waist panel will show the same colour both on the inside of the product and on the outside of the products.

In this way, the presence of the absorbent core can be indicated to the user without the need of providing print or other indications on the topsheet 416 itself.

If a separate piece of material for forming standing gather or leg elastic is attached to the topsheet in the area of the surrounding zone the measurements should be made to a portion where the topsheet is provided, that is shown. This can for example be in the front or the back of the pant article, since usually standing gathers and leg elastics are only attached on the sides of the absorbent in the crotch portion. The separate piece of material for forming standing gather or leg elastic is advantageously also coloured in the same colour as the other portions for example the outside surface, i.e. having a colour differences ΔE*ab less than 10.

All the above examples are absorbent products which are fully coloured, i.e. they have a base colour which they have a base colour which consist of a primary colour such as black, red, blue, violet, orange, yellow, green and indigo, as well as any other hue or mix thereof. These colours may also be mixed with white. The sheets of material both the non-woven and plastic films are fully coloured i.e. they also have a base colour which consist of a primary colour such as black, red, blue, violet, orange, yellow, green and indigo, as well as any other hue or mix thereof. These colours may also be mixed with white.

As stated previously the colour can be added to the material either upon manufacture of it, for example by impregnating, or supplied afterwards by known print techniques.

A fully coloured pant may additional have a discrete graphic, such as flowers, printed for example on the outside surface. In this case the background colour and not the graphic shall be measured.

The invention claimed is:

1. A disposable pant article having a waist portion which in use surrounds a user's waist and a crotch portion connecting front and back portions of the waist portion, the crotch portion comprising an absorbent core for absorbing body exudates and a liquid-permeable topsheet which in use faces a user's crotch, the topsheet covering the absorbent core;

wherein the article has an inside surface which in use faces the user's skin and an outside surface which is opposite the inside surface and in use faces the user's clothing, wherein the article is composed of a plurality of fabrics which define the colours of the inside and outside surfaces of the article, the liquid-permeable topsheet being one of the fabrics;

wherein an absorption zone is defined as a part of the inside surface, on the topsheet, under which the absorbent core is located, and wherein a surrounding zone is defined as a part of the inside surface, on the topsheet, adjacent to and at least partly surrounding the absorption zone;

wherein at least the outside surface and said surrounding zone have, in the CIE L*a*b* colour space, L* values less than 80 and mutual colour differences ΔE*ab less than 10;

wherein the absorbent core or upper layer thereof has an L* value of more than 90; and wherein the absorbent core or upper layer thereof is visible through the topsheet such that the absorption zone has, as a result of the combination of colours of the absorbent core and the topsheet, in the CIE L*a*b* colour space, an L* value less than 90 and a colour difference ΔE*ab more than 5 with respect to said surrounding zone or said outside surface.

2. The disposable pant article according to claim 1, wherein the absorption zone has a colour difference ΔE*ab more than 10 with respect to said surrounding zone or said outside surface.

3. The disposable pant article according to claim 1, wherein the absorption zone has a colour difference ΔE*ab less than 40 with respect to said surrounding zone or said outside surface.

4. The disposable pant article according to claim 1, wherein the absorption zone, as a result of the combination of the colours of the absorbent core and the topsheet, has a higher L* value than said surrounding zone, ΔL* being more than 5.

5. The disposable pant article according to claim 1, wherein said outside surface consists of outside surface portions and said inside surface consists of inside surface portions and all the outside and inside surface portions, except for said absorption zone, have L* values less than 80 and mutual colour differences ΔE*ab less than 10.

6. The disposable pant article according to claim 1, wherein said outside surface consists of outside surface portions and said inside surface consists of inside surface portions and all the outside and inside surface portions, except for said absorption zone, have L* values less than 60 and mutual colour differences ΔE*ab less than 10.

7. The disposable pant article according to claim 1, wherein said outside surface consists of outside surface portions and said inside surface consists of inside surface portions, said absorption zone and said surrounding zone being among said inside surface portions, wherein said outside surface portions and said surrounding zone have L* values less than 60 and mutual colour differences ΔE*ab less than 10 and wherein said inside surface portions other than said absorption zone and said surrounding zone have higher L* values than said outside surface portions.

8. The disposable pant article according to claim 1, wherein the absorption zone has, in the CIE L*a*b* colour space, an L* value less than 90 and a colour difference ΔE*ab more than 5 with respect to said surrounding zone and said outside surface.

9. A disposable pant article having a waist portion which in use surrounds a user's waist and a crotch portion connecting front and back portions of the waist portion, the crotch portion comprising an absorbent core for absorbing body exudates, a liquid-permeable topsheet which in use faces a user's crotch, and a liquid-impermeable backsheet which in use faces the user's clothing, the topsheet covering the absorbent core;

wherein the article has an inside surface consisting of inside surface portions which in use faces the user's skin and an outside surface consisting of outside surface portions which is opposite the inside surface and in use faces the user's clothing;

wherein the inside and outside surface portions of the article are each composed of a plurality of fabrics which define the colours of the inside and outside surface portions, respectively, of the article, the liquid-permeable topsheet and the liquid-impermeable backsheet each being one of the fabrics;

wherein the plurality of fabrics of the outside portions have, in the CIE L*a*b* colour space, L* values less than 80 and mutual colour differences ΔE*ab less than a predetermined limit;

wherein the plurality of fabrics of the inside portions have, in the CIE L*a*b* colour space, an L* value less than 90 and mutual colour difference ΔE*ab more than said predetermined limit; and wherein the absorbent core or upper layer thereof has an L* value of more than 90.

10. The disposable pant article of claim 9, wherein said predetermined limit is 10.

11. The disposable pant article according to claim 9, wherein an absorption zone is defined as a part of the inside surface, on the topsheet, under which the absorbent core is located, and wherein a surrounding zone is defined as a part of the inside surface, on the topsheet, adjacent to and at least partly surrounding the absorption zone.

12. The disposable pant article according to claim 11, wherein the absorption zone has a colour difference ΔE*ab more than 10 with respect to said surrounding zone and/or said outside surface.

13. The disposable pant article according to claim 11, wherein the absorption zone has a colour difference ΔE*ab less than 40 with respect to said surrounding zone or said outside surface.

14. The disposable pant article according to claim 13, wherein the absorption zone, as a result of the combination of the colours of the absorbent core and the topsheet, has a higher L* value than said surrounding zone, ΔL* being more than 5.

15. The disposable pant article according to claim 9, wherein:

an absorption zone is defined as a part of the inside surface, on the topsheet, under which the absorbent core is located, and wherein a surrounding zone is defined as a part of the inside surface, on the topsheet, adjacent to, and at least partly surrounding, the absorption zone; and all the inside and outside surface portions, except for said absorption zone, have L* values less than 80 and mutual colour differences ΔE*ab less than 10.

16. The disposable pant article according to claim 9, wherein:

an absorption zone is defined as a part of the inside surface, on the topsheet, under which the absorbent core is located, and wherein a surrounding zone is defined as a part of the inside surface, on the topsheet, adjacent to, and at least partly surrounding, the absorption zone; and all the inside and outside surface portions, except for said absorption zone, have L* values less than 60 and mutual colour differences ΔE*ab less than 10.

17. The disposable pant article according to claim 9, wherein:

an absorption zone is defined as a part of the inside surface, on the topsheet, under which the absorbent core is located, and wherein a surrounding zone is defined as a part of the inside surface, on the topsheet, adjacent to, and at least partly surrounding, the absorption zone; and all the outside surface portions have L* values less than 60 and mutual colour differences ΔE*ab less than 10 and wherein all the inside surface portions other than the absorption zone and the surrounding zone have higher L* values than said outside surface portions.

18. A method for manufacturing a plurality of disposable pant articles, wherein each article comprises a waist portion which in use surrounds a user's waist and a crotch portion connecting front and back portions of the waist portion, the crotch portion comprising an absorbent core for absorbing body exudates, a liquid-permeable topsheet which in use faces a user's crotch, the topsheet covering the absorbent core, and a liquid-impermeable backsheet which in use faces the user's clothing, wherein each of the articles has an inside surface and an outside surface, the method comprising the steps of:

composing each of the inside surfaces and the outside surfaces of the articles from a plurality of fabrics which define the colours of inside and outside surfaces of the articles, the liquid-permeable topsheet and the liquid-impermeable backsheet each being made from one of said fabrics, the fabrics having colours which are chosen such that:

at least the plurality of fabrics of the outside surfaces of all of said plurality of articles have, in the CIE L*a*b* colour space, L* values less than 80 and mutual colour differences ΔE*ab less than 10;

for all of said plurality of articles, a surrounding zone of the inside surface, which is a part on the topsheet which at least partly surrounds an absorption zone where the absorbent core is located underneath, also has an L* value less than 80 and a mutual colour difference ΔE*ab less than 10 with the outside surface of the respective article;

for all of said plurality of articles, the absorbent core or upper layer thereof has an L* value of more than 90; and for all of said plurality of articles, the absorbent core or upper layer thereof is visible through the topsheet such that the absorption zone has, as a result of the combination of colours of the absorbent core and the topsheet, an L* value less than 90 and a colour difference ΔE*ab more than 5 with respect to the surrounding zone or the outside surface of the respective article.

19. The method of claim 18, wherein all of said plurality of fabrics, except those used for forming layers of the absorbent core, have substantially the same colour.

\* \* \* \* \*